United States Patent [19]

Sinclair et al.

[11] Patent Number: 5,444,113

[45] Date of Patent: * Aug. 22, 1995

[54] END USE APPLICATIONS OF BIODEGRADABLE POLYMERS

[75] Inventors: Richard G. Sinclair, Columbus; Edward S. Lipinsky, Worthington; James D. Browning; Donald Bigg, both of Columbus, all of Ohio; Thomas A. Rogers, Golden, Colo.

[73] Assignee: Ecopol, LLC, Golden, Colo.

[*] Notice: The portion of the term of this patent subsequent to Jan. 19, 2010 has been disclaimed.

[21] Appl. No.: 128,520

[22] Filed: Sep. 29, 1993

Related U.S. Application Data

[63] Continuation-in-part of Ser. No. 950,854, Sep. 22, 1992, which is a continuation-in-part of Ser. No. 579,000, Sep. 6, 1990, Pat. No. 5,216,050, Ser. No. 579,005, Sep. 6, 1990, Pat. No. 5,180,765, Ser. No. 579,460, Sep. 6, 1990, Pat. No. 5,252,642, and Ser. No. 579,465, Sep. 6, 1990, which is a continuation-in-part of Ser. No. 387,670, Jul. 31, 1989, abandoned, which is a continuation-in-part of Ser. No. 229,939, Aug. 8, 1988, abandoned, said Ser. No. 579,000, is a continuation-in-part of Ser. No. 387,676, Jul. 31, 1989, abandoned, which is a continuation-in-part of Ser. No. 229,894, Aug. 8, 1988, abandoned, said Ser. No. 579,005, is a continuation-in-part of Ser. No. 387,678, Jul. 31, 1989, abandoned, which is a continuation-in-part of Ser. No. 229,896, Aug. 8, 1988, abandoned, said Ser. No. 579,460, is a continuation-in-part of Ser. No. 386,844, Jul. 31, 1989, abandoned, which is a continuation-in-part of Ser. No. 317,391, Mar. 1, 1989, abandoned.

[51] Int. Cl.$^6$ ............................................. C08K 5/10
[52] U.S. Cl. .................... 524/306; 524/310; 524/315; 524/317; 524/320; 523/124; 528/354; 528/361
[58] Field of Search ............ 524/306, 310, 315, 317, 524/320; 523/124; 528/354, 361

[56] References Cited

U.S. PATENT DOCUMENTS

| | | | |
|---|---|---|---|
| 2,703,316 | 3/1955 | Schneider | 260/78.3 |
| 2,768,973 | 10/1956 | Castle et al. | 260/602 |
| 3,268,486 | 8/1966 | Klootwijk | 260/78.3 |
| 3,636,956 | 1/1972 | Schneider | 128/335.5 |
| 3,755,558 | 8/1973 | Scribner | 424/47 |
| 3,773,737 | 11/1973 | Goodman et al. | 260/78 A |
| 3,773,919 | 11/1973 | Boswell et al. | 424/19 |
| 3,784,585 | 1/1974 | Schmitt et al. | 260/861 |
| 3,797,499 | 3/1974 | Schneider | 128/334 |
| 3,844,987 | 10/1974 | Clendinning et al. | 260/7.5 |
| 3,867,190 | 2/1975 | Schmitt et al. | 117/138.8 A |
| 3,887,699 | 6/1975 | Yolles | 424/19 |

(List continued on next page.)

FOREIGN PATENT DOCUMENTS

| | | |
|---|---|---|
| 863673 | 2/1971 | Canada . |
| 0108933A1 | 5/1984 | European Pat. Off. . |

(List continued on next page.)

OTHER PUBLICATIONS

Alen et al., "Condensation of Glycolic, Lactic and 2-Hydroxybutanoic Acids during Heating and Identification of the Condensation Products by GLC-MS", pp. 633-636, 1980, *Acta Chem. Scand.*, B34, No. 9.

(List continued on next page.)

*Primary Examiner*—Paul R. Michl
*Assistant Examiner*—Edward J. Cain
*Attorney, Agent, or Firm*—Sheridan Ross & McIntosh

[57] ABSTRACT

Disclosed are products made of degradable materials which include a hydrolytically degradable polymer. The degradable materials can be internally or externally modified. The internally modified polymer composition has polymers modified by the use of comonomers having a relatively high molecular weight. The externally modified polymer composition includes a modifier, wherein the modifier is compatible with the polymer and the modifier is nontoxic, nonvolatile and nonfugitive. The various degradable materials include films, fibers, extruded and molded products, laminates, foams, powders, nonwovens, adhesives and coatings. The disclosed materials are particularly useful for the production of a variety of products in high volumes which are suitable for recycling after use or which are discarded into the environment in large volumes.

22 Claims, No Drawings

U.S. PATENT DOCUMENTS

| | | | |
|---|---|---|---|
| 3,960,152 | 6/1976 | Augurt et al. | 128/335.5 |
| 4,057,537 | 11/1981 | Sinclair | 260/78.3 |
| 4,300,565 | 11/1981 | Rosensaft et al. | 128/335.5 |
| 4,379,138 | 4/1983 | Pitt et al. | 424/78 |
| 4,419,340 | 12/1983 | Yolles | 424/19 |
| 4,526,938 | 7/1985 | Churchill et al. | 525/415 |
| 4,539,981 | 9/1985 | Tunc | 128/92 |
| 4,550,449 | 11/0585 | Tunc | 623/16 |
| 4,643,734 | 2/1987 | Lin | 623/16 |
| 4,675,189 | 6/1987 | Kent et al. | 424/490 |
| 4,745,160 | 5/1988 | Churchill et al. | 525/415 |
| 4,750,492 | 6/1988 | Jacobs | 128/335 |
| 4,761,289 | 8/1988 | Shalati et al. | 424/468 |
| 4,788,979 | 12/1988 | Jarrett et al. | 128/335.5 |
| 4,800,219 | 1/1989 | Murdoch et al. | 525/413 |
| 4,835,293 | 5/1989 | Bhatia | 549/274 |
| 4,891,263 | 1/1990 | Kotliar et al. | 428/225 |
| 4,897,268 | 1/1990 | Tice et al. | 424/422 |
| 4,933,182 | 6/1990 | Higashi et al. | 424/435 |
| 4,942,035 | 7/1990 | Churchill et al. | 424/423 |
| 4,960,866 | 10/1990 | Bendix et al. | 528/499 |
| 4,961,707 | 10/1990 | Magnusson et al. | 433/215 |
| 4,981,696 | 1/1991 | Loomis et al. | 424/486 |
| 4,990,222 | 2/1991 | Aigner et al. | 203/91 |
| 5,028,667 | 7/1991 | McLain et al. | 525/415 |
| 5,051,272 | 9/1991 | Hermes et al. | 427/2 |
| 5,053,485 | 10/1991 | Nieuwenhuis et al. | 528/354 |
| 5,053,522 | 10/1991 | Muller | 549/274 |
| 5,066,231 | 11/1991 | Oxman et al. | 433/214 |
| 5,066,772 | 11/1991 | Tang et al. | 528/354 |
| 5,068,220 | 11/1991 | Vanderbilt et al. | 514/3 |
| 5,076,807 | 12/1991 | Bezwada et al. | 606/230 |
| 5,076,983 | 12/1991 | Loomis et al. | 264/101 |
| 5,077,049 | 12/1991 | Dunn et al. | 424/426 |
| 5,080,665 | 1/1992 | Jarrett et al. | 606/219 |
| 5,084,051 | 1/1992 | Törmälä et al. | 606/77 |
| 5,085,629 | 2/1992 | Goldberg et al. | 604/8 |
| 5,089,632 | 2/1992 | Paul | 549/274 |
| 5,134,171 | 7/1992 | Hammel et al. | 521/98 |
| 5,138,074 | 8/1992 | Bellis et al. | 549/274 |
| 5,180,765 | 1/1993 | Sinclair | 524/306 |
| 5,196,551 | 3/1993 | Bhatia et al. | 549/274 |
| 5,235,031 | 8/1993 | Drydale et al. | 528/354 |
| 5,236,560 | 8/1993 | Drysdale et al. | 203/99 |
| 5,254,718 | 10/1993 | Anton et al. | 560/55 |
| 5,274,127 | 12/1993 | Sinclair et al. | 549/274 |

FOREIGN PATENT DOCUMENTS

| | | |
|---|---|---|
| 0261572 | 3/1988 | European Pat. Off. |
| 0266119A2 | 5/1988 | European Pat. Off. |
| 0406015A1 | 1/1991 | European Pat. Off. |
| 8901718 | 11/1990 | South Africa |
| 755447 | 8/1956 | United Kingdom |
| 1122229 | 7/1968 | United Kingdom |
| 2216411 | 10/1989 | United Kingdom |
| 2223027 | 3/1990 | United Kingdom |
| WO86/00533 | 1/1986 | WIPO |
| WO88/04557 | 6/1988 | WIPO |
| WO90/01521 | 2/1990 | WIPO |
| WO91/17155 | 11/1991 | WIPO |
| WO92/01548 | 2/1992 | WIPO |
| WO92/01737 | 2/1992 | WIPO |
| WO92/04410 | 3/1992 | WIPO |
| WO92/04412 | 3/1992 | WIPO |
| WO92/05311 | 4/1992 | WIPO |
| WO92/12228 | 7/1992 | WIPO |
| WO93/04112 | 3/1993 | WIPO |

OTHER PUBLICATIONS

Barrows, "Degradable Implant Materials: a review of synthetic absorbable polymers and their applications", pp. 233–247, 186, *Clinical Materials*, vol. 1.

Bezzi, "Transformation of Cyclic Esters into linear Polyesters", pp. 215–224, 68.

Deïbig, et al., "Polytetramethyl Glycolide I. Synthesis and Properties of Polytetramethyl Glycolide", pp. 123–131, 197, *Die Makromolekulare Chemie*, 145 (Nr. 3630).

Deïbig, et al., "Polytetramethyl Glycolide II. Thermal Behavior of Polytetramethyl Glycolide", pp. 133–139, 1971, *Die Makromolekulare Chemie*, 145 (Nr. 3631).

Ennis, "Degradability Additives", pp. 163–164, *Modern Plastics*, Encyclopedia 92, Mid–Oct.

Fukuzaki et al., "Low-Molecular-Weight Copolymers Composed of L-lactic Acid and Various DL-hydroxy Acids as Biodegradable Carriers", pp. 2571–2577, 1989, *Makromol. Chem.*, 190.

Fukuzaki et al., "Synthesis of Biodegradable Poly(-L-latic Acid-co-D,L,-mandelic Acid) with Relatively Low Molecular Weight", pp. 2407–2415, 1989, *Makromol. Chem.*, 190.

Kricheldorf et al., "Polylactones 3. Copolymerization of glycolide with L,L-Lactide and Other Lactones", pp. 25–38, 1985, *Makromol. Chem., Suppl.*, vol. 12.

Kricheldorf et al., "Polylactones. 13. Transesterification of Poly(L-Lactide) With Poly(Glycolide), Poly(-$\beta$-Propio-Lactone), and Poly($\epsilon$-Caprolactone)", pp.

(List continued on next page.)

OTHER PUBLICATIONS

1345–1356, 1987, *J. Makromol. Sci.-Chem.*, vol. A24-(II).

Pitt et al., "Sustained Drug Delivery Systems" I. The Permeability of Poly($\epsilon$-Caprolactone), Poly(DL-Lactic Acid), and Their Copolymers, pp. 497–507, 1979, *Jour. of Bio. Mat. Res.*, vol. 13.

Schindler et al., "Biodegradable Polymers For Sustained Drug Delivery", pp. 251–286, 1977, in *Contemporary Topics in Polymer Science*, vol. 2.

Wehrenberg, "Lactic Acid Polymers: Strong, Degradable Thermoplastics", pp. 63–66, 1981, Sept.

Wiley, "Synthesis and Evaluation of Biodegradable Block Copolymers of $\epsilon$-Caprolactone and D L-Lactide", pp. 593–600, 1983, *Jour. of Poly. Sci.: Poly. Letters Ed.*, vol. 21.

Wise, "Biopolymeric Controlled Release Systems", pp. 3–28, 1984, vol. I.

END USE APPLICATIONS OF BIODEGRADABLE POLYMERS

REFERENCE TO RELATED APPLICATIONS

The present application is a continuation-in-part of U.S. patent application Ser. No. 07/950,854, filed Sep. 22, 1992 entitled "Degradable Polymer Composition"; which is a continuation-in-part of U.S. patent application Ser. No. 07/579,000 filed Sep. 6, 1990 now U.S. Patent No. 5,216,050, issued Jun. 1, 1993, entitled "Blends of Polylactic Acid"; and U.S. patent application Ser. No. 07/579,005 filed Sep. 6, 1990 now U.S. Pat. No. 5,180,765, issued Jan. 19, 1993, entitled "Biodegradable Packaging Thermoplastics from Polylactic Acid"; and of pending U.S. patent application Ser. Nos. 07/579,460, entitled "Degradable Impact Modified Polylactic Acid"; and 07/579,465, entitled "Biodegradable Replacement of Crystal Polystyrene"; all filed on Sep. 6, 1990; which are continuation-in-parts of U.S. patent application Ser. Nos. 07/387,676; 07/387,678; 07/386,844; and 07/387,670; respectively, all filed on Jul. 31, 1989, and now abandoned; which are continuations-in-part of U.S. patent application Ser. Nos. 07/229,894, filed Aug. 8, 1988; 07/229,896, filed Aug. 8, 1988; 07/317,391, filed Mar. 1, 1989; and 07/229,939, filed Aug. 8, 1988; respectively, all now abandoned; and all of which are incorporated by reference herein in their entirety.

FIELD OF THE INVENTION

The invention relates to degradable polymer compositions and processes for forming various degradable materials including those compositions. The compositions and processes are useful for the production of a variety of products.

BACKGROUND OF THE INVENTION

Some polymers are known to degrade by hydrolysis in the presence of water and thereby decompose to smaller chemical units. Some of these polymers are also biodegradable, such as polylactic acid and polyglycolic acid. Polymers such as polylactic acid and polyglycolic acid can be referred to generally as polydioxanediones because each is prepared by polymerization of a dioxanedione-based monomer. As used herein, except as specifically noted otherwise, dioxaneone refers to compounds having a dioxane ring with at least one carbonyl oxygen pendant from the dioxane ring. The remaining three carbon atoms in the dioxane ring may have various constituents pendant therefrom. Although the term dioxaneone, which is also sometimes written as dioxanone, is often used in a specific sense to refer to 2-keto-1,4-dioxane, dioxaneone is used herein in a general sense as discussed below, unless otherwise specifically indicated by the general formula:

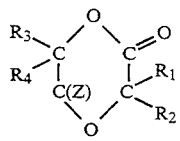

where $R_1$, $R_2$, $R_3$ and $R_4$ can be any of a variety of constituents and where Z can be one or more constituents covalently bonded to the associated carbon atom in the dioxane ring. When all of $R_1$, $R_2$, $R_3$ and $R_4$ are hydrogen and Z is two hydrogen constituents, then the compound is 2-keto-1,4-dioxane.

Dioxaneones such as lactide and glycolide, in which Z is a carbonyl oxygen, may be more specifically referred to as dioxanediones since they each have two carbonyl oxygens pendant from the dioxane ring. Dioxanediones are cyclic diesters that may be represented by the general formula:

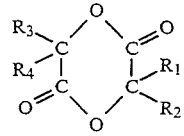

Where $R_1$, $R_2$, $R_3$ and $R_4$ can be any of a variety of constituents. When $R_1$, $R_2$, $R_3$, and $R_4$ are all hydrogen, then the compound is glycolide which is also referred to as 1,4-dioxane-2,5-dione. Although the term dioxanedione is sometimes used to refer specifically to glycolide, the term as used herein is always employed in the general sense to indicate a class of compounds as indicated by the generic formula above, except as otherwise noted herein. When $R_1$ and $R_3$ are methyl and $R_2$ and $R_4$ are hydrogen the compound is lactide, which may be also referred to as 3,6-dimethyl-1,4-dioxane-2,5-dione. A polydioxaneone having one or more repeating units representative of a dioxanedione monomer may be more specifically referred to as a polydioxanedione. When a dioxaneone contains one or more asymmetrical carbon atoms, such as is the case with lactide, then that particular dioxaneone can exist as various optical isomers. For example, lactide can exist as two optically active isomers, D-lactide and L-lactide, or as the optically inactive isomer meso-lactide. D-lactide and L-lactide can also be present in equal quantities to form an optically inactive mixture known as racemic-lactide. Both meso-lactide and racemic-lactide are often designated as simply D,L-lactide.

Higher molecular weight polymers can be produced by ring-opening polymerization of dioxanedione monomers. Dioxanediones used as monomers to produce higher molecular weight polymers have traditionally been made from low molecular weight poly-$\alpha$-hydroxycarboxylic acids by a depolymerization reaction often referred to as "backbiting." The backbiting process is relatively expensive, contributing to the lack of feasibility in developing low-cost consumer products for mass-market applications using polydioxanedione polymers.

Due to the expense and difficulty in preparing hydrolytically degradable polymers such as polydioxanedione, their use has been largely confined to high value medical applications where bioabsorbable materials are required. Most reported medical applications involve internal use of the polymers, such as for sutures, prosthetic devices, and drug release matrices. Some polymers that have received considerable attention for medical applications include polylactic acid, polyglycolic acid, poly-$\epsilon$-caprolactone and polydioxanone.

Some attempts have been made in the medical field to vary properties of bioabsorbable polymers based on the specific intended use. Properties that have received some attention include strength, flexibility, and rate of hydrolytic degradation. It is generally known that a copolymer usually exhibits different properties from homopolymers of either individual comonomer. Some attempts have been made to develop specific copolymers for specific medical applications.

Many references, however, identify several possible comonomers without any consideration for the possible effects that such comonomers might have on properties of the copolymer. For example, U.S. Pat. No. 2,703,316 by Schneider, issued Mar. 1, 1955, discusses lactide polymers and copolymers capable of being formed into a tough, orientable, self-supporting thin film with up to 50% of another polymerizable cyclic ester having a 6- to 8-membered ring. The patent specifically discloses polymerization of 5 parts lactide and 5 parts glycolide and also polymerization of 12 parts lactide and 2 parts tetramethylglycolide, but also provides an extensive list of other possible comonomers with no elaboration on polymer properties.

A few references have suggested the use of hydrolytically degradable polymers outside of the medical field. For example, U.S. Pat. No. 4,057,537 by Sinclair, issued Nov. 8, 1977, discusses copolymers of L-lactide and ε-caprolactone prepared from a mixture of comonomers containing from about 50 to about 97 weight percent L-lactide and the remainder ε-caprolactone. Strength and elasticity are shown to vary depending on the relative amounts of L-lactide and ε-caprolactone monomers. Depending upon the L-lactide/ε-caprolactone ratio, the polymers are disclosed to be useful for the manufacture of films, fibers, moldings, and laminates. However, no specific applications are discussed. Sinclair discloses that plasticizers may be added to the copolymer if desired, but provides no guidance concerning what compounds might be suitable. Lipinsky et al , 1986, pp. 26–32, "Is Lactic Acid a Commodity Chemical," *Chemical Engineering Process,* August, discloses the use of polylactic acid for packaging material without discussing modifications of material properties by inclusion of plasticizers or other components.

Although it has been noted that suitable compounds, such as plasticizers, may be added to modify the properties of some hydrolytically degradable polymers, such as in U.S. Pat. No. 4,057,537 just discussed, little guidance has been given as to what compounds might be effective. Identifying suitable compounds for use in externally modifying and identifying suitable comonomers for internally modifying the properties of biodegradable polymers has been a major problem confronted in developing biodegradable polymers for mass-marketed products. Relatively few references discuss modification of properties of hydrolytically degradable polymers with external compounds, such as polylactide homopolymers and copolymers. The medical industry has generally sought to tailor polymer compositions to specific medical applications by developing specific copolymers, rather than to add external compounds. Those references that do discuss compounds, such as plasticizers, however, offer little guidance in selecting suitable compounds to be used for mass-marketed, hydrolytically degradable polymer products.

Compounds which effectively modify properties of polymer products are not to be confused with compounds that are designed only to aid polymer processing and that are removed prior to or during manufacture of the final product. Compounds which are effective in modifying properties of polymer products should be completely miscible with the polymer, nonvolatile, and should not migrate to the surface of the polymer composition, as might be desirable with a processing aid.

Plasticizers or other similar compounds used in mass-marketed products made of hydrolytically degradable polymers will be deposited into the environment in large quantities upon degradation of the polymers. Therefore even low levels of toxicity are a concern due to the potentially huge quantity of potential waste.

Thus, a need exists for degradable polymer compositions that are suitable for use with products that can replace existing non-degradable products that are rapidly becoming difficult to dispose of due to limited landfill space and other environmental concerns.

SUMMARY OF THE INVENTION

The present invention is directed toward a variety of products which are made of degradable materials. The degradable materials include a hydrolytically degradable polymer, such as polylactic acid. The hydrolytically degradable polymer can either be an externally or an internally modified polymer. The internally modified polymer is modified by the inclusion of other comonomers in the polymer molecule as described in more detail below. The externally modified polymer composition includes a modifier that is compatible with the polymer and is nontoxic, nonvolatile and nonfugitive. The polymer and modifier are compatible with each other and typically have solubility parameters which are within about 1.0 (calorie per cubic centimeter)$^{0.5}$ of each other and the solubility parameters are typically between about 7.5 and about 16.5 (calories per cubic centimeter)$^{0.5}$. The modifier is nonvolatile and typically has a vapor pressure of less than about 50 Torr at 180° C. and a boiling temperature above about 280° C. at 1 atmosphere.

The degradable materials of the present invention are useful for the production of commercial and consumer products. Such products include, for example, products for controlled release of chemicals, oral drug delivery products, automobile products, gardening products, consumer products, health products, substrates that are suitable for the attachment and growth of living cells, construction products, adhesive products, absorbent articles, flammable products, lubricants, bags, netting, rope, coatings, filters, inks, containers, packaging, clothing, and paper goods. The degradable materials of the present invention are particularly useful for the production of frequently littered products, such as drink containers, labels, food packaging, printed matter, construction material and vehicle supplies.

DETAILED DESCRIPTION OF THE INVENTION

The present invention is directed toward a variety of products which are made of degradable materials. The degradable materials can include either or both of an externally or an internally modified polymer composition, as those terms are described below.

DEGRADABILITY

As used herein, the term "degradable," with reference to the various materials of the present invention refers to a material including a degradable polymer as described below and in the proportions described below. The term "degradable," with reference to the polymer, refers to a polymer having a polymer molecular structure which can decompose to smaller molecules. As discussed below, the degradable polymer can be hydrolytically degradable in which water reacts with the polymer to form two or more molecules from the polymer.

The polymer of the present materials is further characterized as being degradable within a time frame in which products made from the materials, after use, can either be readily recycled by decomposition of the polymer into its monomeric units or, if disposed of in the environment, such as in landfills, the polymer degrades quickly enough to avoid significant accumulation of discarded products or wherein the rate of accumulation is significantly less than that of similar products which are not degradable. The materials of this invention degrade in a time period of a few months to a few years, whereas similar mass-produced, nondegradable products require, typically, decades to centuries.

The degradation characteristics of the polymer in the present materials depend in large part on the type of material being made with the polymer. Thus, the polymer needs to have suitable degradation characteristics so that when processed and produced into a final material, the material does not undergo significant degradation until after the useful life of the material. Therefore, different embodiments of the present invention will have different degradation characteristics. The timing of degradation of the materials can be evaluated by accelerated short-term testing under which materials are exposed to harsh conditions. For example, a useful test for degradation is an accelerated short-term test in which materials are subjected to a temperature of 95° F. (35° C.) and 95% humidity. Under these conditions, in a preferred embodiment, a test sample of material which is in the configuration of a 1-3 mil film is considered to be degradable if it becomes sticky to the touch, cloudy, opaque or embrittled typically in less than about three months. Under these same conditions, in a preferred embodiment, a test sample of material which is in the configuration of a 1-3 mil film is considered to be degradable if it has a tensile strength loss or a molecular weight loss of at least about 90% in less than about six months.

The polymer of the present invention can also be used to produce articles which, because the articles require durability in the use for which the article is designed (e.g., tires and hospital supplies), are not degradable under ambient conditions within the time frame of the useful life of the article. As such, in another aspect of the present invention, the polymer can be used to produce such durable articles. Such articles are, nonetheless, considered to be degradable and are particularly useful because they can be treated to accelerate degradation and therefore are degradable upon demand. For example, the polymer can be exposed to environmental conditions which accelerate degredation as, for example, being treated with increased temperature, and/or increased pressure, and/or increased humidity, and/or exposed to suitable catalysts.

The polymer of the present invention can be characterized as being hydrolytically degradable. As used herein, the term "hydrolytically degradable" refers to a composition in which chemical bonds in the molecule are subject to hydrolysis, thus producing smaller molecules. In a further embodiment of the present invention, the polymer is biodegradable. Biodegradability refers to a compound which is subject to enzymatic decomposition, such as by microorganisms, or a compound, portions of which are subject to enzymatic decomposition, such as by microorganisms. In one instance, for example, a polymer such as polylactic acid can be degraded by hydrolysis to individual lactic acid molecules which are subject to enzymatic decomposition by a wide variety of microorganisms. Microorganisms typically can consume hydroxycarboxylic acid-containing oligomers with molecular weights of up to about 1000 daltons, and preferably up to about 600 daltons, depending on the chemical and physical characteristics of the oligomer.

EXTERNALLY MODIFIED POLYMER COMPOSITION

Polymers

The polymer of the present composition can be an externally modified polymer and can be selected from a variety of nontoxic degradable polymers. Typically, the polymer should have a weight average molecular weight of between about 5,000 and about 1,500,000. Appropriate molecular weights will vary according to desired material type and will be discussed more fully below. The polymer of the present composition can be a homopolymer, a copolymer, or a physical blend of homopolymers and/or copolymers. Typically, the polymer of the present materials includes repeating monomer or comonomer units which are selected from the following group and which polymers are non-toxic and degradable:

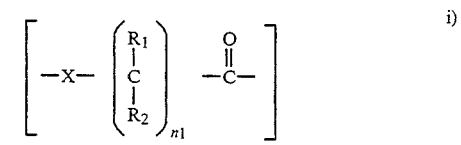

i)

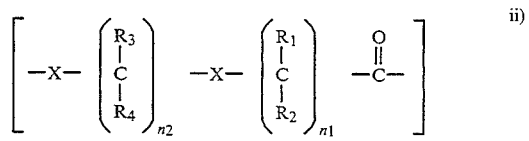

ii)

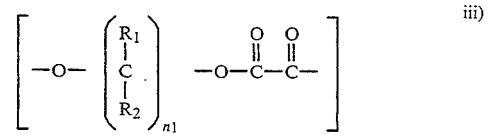

iii)

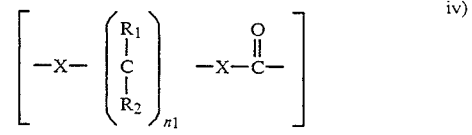

iv)

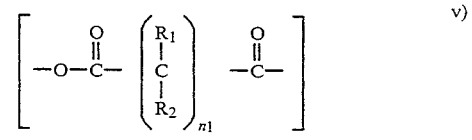

v)

wherein X is the same or different and is O or NR' with R' independently being H, hydrocarbyl, or substituted hydrocarbyl; $R_1$, $R_2$, $R_3$ and $R_4$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1-12.

The polymer of the present invention typically includes the above repeating monomer or comonomer units in an amount of at least about 5 weight percent, more preferably at least about 10 weight percent and more preferably at least about 20 weight percent. Preferably, the polymer includes a high enough percentage of polymerized monomers which are hydrolytically degradable so that, upon degradation, polymer fragments of less than about 600 molecular weight are produced because such polymer fragments are small enough to be metabolized by microorganisms.

The nontoxic degradable polymer of the present materials can be more particularly characterized as having repeating monomer or comonomer units selected from the group consisting of:

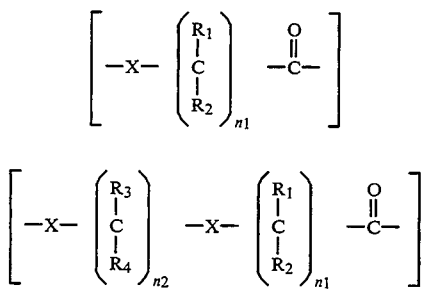

wherein X is the same or different and is O or NR' with R' independently being H, hydrocarbyl, or substituted hydrocarbyl; $R_1$ and $R_2$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1–12.

The polymer of the present materials is more particularly characterized as comprising repeating monomer or comonomer units derived from monomers selected from the group consisting of alpha-hydroxycarboxylic acids, beta-hydroxycarboxylic acids, gamma-hydroxycarboxylic acids, delta-hydroxycarboxylic acids, epsilon-hydroxycarboxylic acids, beta-lactones, gamma-lactones, delta-lactones, epsilon-lactones, beta-lactams, gamma-lactams, delta-lactams, epsilon-lactams, cyclic diesters of alpha-hydroxycarboxylic acids, dioxanones, substituted variations of the foregoing compounds, and combinations thereof. The polymer of the present materials is further characterized as comprising repeating monomer or comonomer units derived from monomers selected from the group consisting of lactic acid, glycolic acid, epsilon-hydroxycaproic acid, lactide, glycolide, epsilon-caprolactone, delta-valerolactone, substituted variations of the foregoing compounds, and combinations thereof.

In a more preferred embodiment, the polymer comprises repeating monomer or comonomer units derived from lactic acid which can be the result of direct polymerization of lactic acid or the polymerization of lactide. Preferably, the polymer typically includes more than about 50 weight percent repeating units derived from lactic acid or lactide, and more preferably greater than about 75 weight percent. In another embodiment, the polymer is prepared from polymerization of a composition including lactide in which greater than about 50% by weight of the lactide is optically active and less than 50% is optically inactive lactide selected from the group consisting of racemic D,L-lactide and meso-lactide.

In a more preferred embodiment of the invention the polymer is polylactic acid and has the repeating units of the formula,

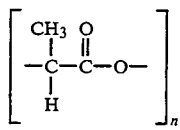

wherein n is the number of repeating units and n is an integer equal to at least about 150 and preferably $150 \leq n \leq 20,000$. Preferably the unoriented composition has the physical properties of: a tensile strength of about 300 to about 20,000 psi, an elongation to failure of about 2 to about 1,000 percent, and a tangent modulus of about 1,000 to about 500,000 psi.

Those skilled in the art will recognize that this wide latitude of properties must be accommodated to serve the varied needs of the plastics industry. A review of this range of properties is found in commonly assigned U.S. Pat. No. 5,180,765, issued Jun. 1, 1993, entitled "Biodegradable Packaging Thermoplastics From Polylactic Acid". For example, presently used commodity thermoplastics vary considerably by use. Stiff thermoforms, such as are used in salad covers are typically served by thermoplastics such as polystyrene, which will be oriented to have a tensile strength of about 7500 psi, and elongation to break of about 4% and an elastic modulus of about 350,000 psi. At the other extreme, pliable films for trash bags use plastics with a tensile strength of about 1500 psi, elongations of 500%, and an elastic modulus of about 25,000 psi.

External Modifiers

The modifier for the externally modified polymer composition of the present materials is a compound which introduces pliability, flexibility and toughness into a polymer composition to an extent that may not be found in the polymer-only composition. Also, addition of modifiers to the polymer composition can reduce the melt viscosity of the polymer and lowers the temperature, pressure, and shear rate required to melt form the polymer. Further, the modifier can add impact resistance to the polymer which is not found in the polymer-only composition. Thus, the modifier of the present materials can be considered as a compatibilizer, flexibilizer or plasticizer.

The modifier is also considered to lower the glass transition temperature ($T_g$) of a polymer. Typically, the modifier of the present materials will modify the $T_g$ of the various materials to varying degrees, depending upon the intended end use of the material. In discussion of various specific embodiments of materials of the present invention, which are discussed below, various $T_g$ parameters are provided.

A further aspect of the present materials is that the modifier component is nonvolatile. Thus, an important characteristic of the present materials is that during polymerization and processing of the materials, the modifier does not volatilize so that subsequent to polymerization and processing of the polymer composition into materials, the modifier substantially remains in the materials. Typically, a nonvolatile modifier refers to a modifier in a polymer/modifier material in which less than about 25 weight percent of the modifier initially present either before polymerization or before processing is lost due to volatilization of the modifier during the production of the material, more preferably less than about 5 weight percent, and even more preferably less than about 1 weight percent. Such modifiers are typically compounds which have a vapor pressure of less than about 50 Torr at 180° C., more preferably less than about 10 Torr at 180° C., and even more preferably less than about 1 Torr at 180° C. Such modifiers typically have a boiling point above about 280° C. at atmospheric pressure, more preferably above about 340° C., and even more preferably above about 400° C.

A further aspect of the nonvolatility of the modifier is that the modifier can be nonvolatile due to strong polar characteristics of the modifier. Such polar characteristics are illustrated by those of the discussion below regarding the role of polar characteristics in compatibility of the polymer and modifier.

Those skilled in the art will recognize the difference between a melt-processing aid and a modifier, such as a plasticizer. A melt-processing aid permits easier processing, i.e., lower processing temperatures and viscosities of the polymer melt, while a modifier imparts an attenuation of certain end-use properties, e.g., modulus. In some instances, it is preferable to have a volatile additive for use as a melt processing aid so that processing is facilitated, and following processing, the additive can be removed by volatilization to allow more desirable strength or other physical property to develop. For example, lactide can be added as a processing aid to polylactide in a twin-screw compounder that transports the melt blend to an extruder where the lactide is removed, either at a later zone or the die of the extruder. In this way, stiff polylactide compositions without a modifier can be melt fabricated without sacrificing processability.

A further aspect of the materials of the present invention is that the modifier is nonfugitive. The term nonfugitive refers to a modifier that does not escape from the material during the useful life of the materials. That is, the modifier remains substantially intimately dispersed in the polymer for the useful life of the material. For example, fugitive materials, which may initially be present as a discrete phase, can become soluble in the polymer and migrate towards the surface of a material to form a surface film or vapor. That is, fugitive modifiers are not compatible with the polymer over time to an extent which impedes the intended function of the material. Typically, modifiers in a polymer/modifier material are considered nonfugitive when less than about 30 weight percent of the modifier present in the processed material is lost due to becoming fugitive during the useful life of the material, that is, during the time period from after the material is processed until the time the ultimate consumer discards the materials, more preferably less than about 10 weight percent and more preferably less than about 1 weight percent.

The modifier is preferably selected from the group consisting of dicarboxylic acids, derivatives of dicarboxylic acids, polyesters of dicarboxylic acids, tricarboxylic acids, derivatives of tricarboxylic acids, polyesters of tricarboxylic acids, cyclic diesters of alpha-hydroxycarboxylic acids, derivatives of cyclic diesters of alpha-hydroxycarboxylic acids, oligomers of cyclic diesters of alpha-hydroxycarboxylic acids, beta-lactones, delta-lactones, gamma-lactones, ϵ-lactones, of alpha-hydroxycarboxylic acids, esters of oligomers of alpha-hydroxycarboxylic acids, benzoic acid derivatives, epoxy derivatives, glycol derivatives, phthalic acid derivatives, phosphoric acid derivatives, ketones, amides, nitriles, and combinations of the foregoing.

The modifier is more preferably selected from the group consisting of adipic acid derivatives, azelaic acid derivatives, cyclic esters of oligomers of lactic acid, esters of oligomers of lactic acid, citric acid derivatives, polyesters of adipic acid, polyesters of azelaic acid, polyesters of sebacic acid, sebacic acid derivatives, benzoic acid derivatives, epoxy derivatives, glycol derivatives, phthalic acid derivatives, phosphoric acid derivatives, and combinations thereof.

The modifier is more preferably selected from the group consisting of di-n-hexyl adipate, bis(2-ethylhexyl)adipate, diisodecyl adipate, bis(2-butoxyethyl)adipate, bis(2-ethylhexyl)azelate, lactide, epsilon-caprolactone, glycolide, delta-valerolactone, oligomeric lactic acid, oligomeric lactic acid ethyl ester, acetylated lactoyllactate ethyl ester, tri-n-butyl citrate, tri-n-butyl acetylcitrate, diethylene glycol dibenzoate, dipropylene glycol dibenzoate, epoxidized soy oil, 2-ethylhexyl epoxy tallate, diethylene glycol dinonanoate, triethylene glycol di(2-ethylbutyrate), pentaerythritol esters, alkoxy sucrose and glucose, acylated sucrose and glucose, alkylated and acylated glycols, starch esters, N-acylated amino acid esters, amide derivatives and oligomers of N-acylated amino acid esters, polyethylene glycol esters, tri(2-ethylhexyl)phosphate, diemethyl phthalate, diethyl phthalate, butyl 2-ethylhexyl phthalate, bis(2-ethylhexyl)phthalate, dicyclohexyl phthalate, diphenyl phthalate, adipic acid polyester with molecular weight from about 190 to about 6000, azelaic acid polyester with molecular weight from about 232 to about 7500, sebacic acid polyester with molecular weight from about 246 to about 8000, di-n-butyl sebacate, and bis(2-ethylhexyl)sebacate, and combinations thereof.

The modifier is more preferably selected from the group consisting of di-n-hexyl adipate, bis(2-butoxyethyl)adipate, bis(2-ethylhexyl)azelate, lactide, epsilon-caprolactone, glycolide, delta-valerolactone, oligomeric lactic acid, oligomeric lactic acid ethyl ester, tri-n-butyl citrate, tri-n-butyl acetylcitrate, dipropylene glycol dibenzoate, epoxidized soy oil, 2-ethylhexyl epoxy tallate, diethylene glycol dinonanoate, triethylene glycol di(2-ethylbutyrate), butyl 2-ethylhexyl phthalate, bis(2-ethylhexyl)phthalate, dicyclohexyl phthalate, adipic acid polyester with molecular weight from about 190 to about 6000, azelaic acid polyester with molecular weight from about 232 to about 7500, sebacic acid polyester with molecular weight from about 246 to about 8000, di-n-butyl sebacate, and combinations thereof.

The modifier is more preferably selected from the group consisting of dicarboxylic acids, derivatives of dicarboxylic acids, polyesters of dicarboxylic acids, tricarboxylic acids, derivatives of tricarboxylic acids, polyesters of tricarboxylic acids, cyclic diesters of alpha-hydroxycarboxylic acids, derivatives of cyclic diesters of alpha-hydroxycarboxylic acids, oligomers of cyclic diesters of alpha-hydroxycarboxylic acids, beta-lactones, delta-lactones, gamma-lactones, ϵ-lactones, oligomers of alpha-hydroxycarboxylic acids, esters of oligomers of alpha-hydroxycarboxylic acids, and combinations of the foregoing.

The modifier is further preferably selected from the group consisting of adipic acid derivatives, azelaic acid derivatives, cyclic esters, oligomers of lactic acid, esters of oligomers of lactic acid, citric acid derivatives, polyesters of adipic acid, polyesters of azelaic acid, polyesters of sebacic acid, sebacic acid derivatives, and combinations thereof.

The modifier is further preferably selected from the group consisting of di-n-hexyl adipate, lactide, epsilon-caprolactone, glycolide, delta-valerolactone, oligomeric lactic acid, oligomeric lactic acid ethyl ester, tri-n-butyl acetylcitrate, adipic acid polyester with molecular weight from about 190 to about 6000, azelaic acid polyester with molecular weight from about 232 to about 7500, and combinations thereof.

In one aspect of the present invention, and particularly when the polymer includes lactic acid-derived repeating units, preferred modifiers include lactic acid, lactide, oligomers of lactic acid, oligomers of lactide and mixtures thereof. The preferred oligomers of lactic acid and oligomers of lactide are defined by the formula:

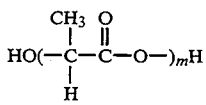

where m is an integer: $2 \leq m \leq 75$. Preferably m is an integer: $2 \leq m \leq 10$.

Further modifiers useful in the invention include oligomeric derivatives of lactic acid and lactide selected from the group defined by the formula:

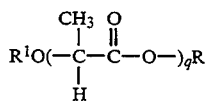

where R=H, alkyl, aryl, alkylaryl or acetyl, and R is saturated, where R'=H, alkyl, aryl, alkylaryl or acyl, and R' is saturated, where R and R' cannot both be H, where q is an integer: $2 \leq q \leq 75$. Preferably, q is an integer: $2 \leq q \leq 10$.

The modifier in the present materials is preferably in an amount greater than about 0.1 weight percent, more preferably greater than about 1 weight percent, more preferably greater than about 5 weight percent, and more preferably greater than about 10 weight percent. Also, the modifier in the present materials is preferably in an amount less than about 60 weight percent, more preferably less than about 50 weight percent, and more preferably less than about 40 weight percent. For purposes of disclosure herein, each of the above minimum values can be associated with each of the maximum values.

Compatibility

A further important characteristic of the present degradable materials is that the modifier and degradable polymer are compatible. A compatible modifier generally refers to a modifier which is intimately dispersible, as that term is defined below, in the polymer and to a polymer which is swellable in the modifier. As used herein, where the modifier is a liquid at the mixing temperature, the term "swellable" means that the polymer will expand in volume to at least about 120% of its initial volume in the presence of excess modifier.

More particularly, the term "compatibility" refers to a modifier which is thermally compatible with the polymer composition such that upon processing and use of the composition, the modifier and polymer remain as uniform mixtures, i.e., one that is not cheesy in appearance and without significant change in the relative proportions of the components. Compatible mixtures typically are clear, non-oily, and the material does not stress craze easily. One useful indicator of the compatibility of a modifier and polymer is the difference between the solubility parameters of the polymer and modifier. The term "solubility parameter" is also referred to as Hildebrand constant and is given in units of energy per volume, such as calories per cubic centimeter (cal/cm$^3$). Solubility parameters can be calculated by known methods shown in the literature. A solubility parameter is a measure of the internal attractive force that molecules of the same compound have for each other. Thus, for two different compounds having similar solubility parameters, the two compounds are likely to be readily as soluble with molecules of the other compound as they are with molecules of the same compound. It should be noted that while solubility parameters are useful in assessing compatibility, they are not absolute predictors. Calculations of solubility parameters, for instance, do not account for all aspects of the chemical structure of a molecule. Thus, chemical features, such as polar character which is discussed below, and others, can make otherwise incompatible species compatible and vice versa.

Typically, the solubility parameters of the polymer and modifier are within about 1.0 cal/cm$^3$, preferably within about 0.75 cal/cm$^3$, and more preferably within about 0.5 cal/cm$^3$. The solubility parameters of the modifier and the polymer are also typically each in the range of from about 7.5 cal/cm$^3$ to about 16.5 cal/cm$^3$, more preferably between about 8.0 cal/cm$^3$ to about 12.0 cal/cm$^3$ and more preferably between about 9.0 cal/cm$^3$ and about 11.0 cal/cm$^3$.

A first parameter for determining compatibility is the difference in solubility parameters between the polymer and the modifier. It has been surprisingly found, however, that polymer/modifier combinations which have solubility parameter differences outside of the parameters discussed above, can be compatible if the polymer and modifiers have suitable polar characteristics which provide sufficient polar attraction between the species to make the polymer and modifier compatible. For example, it has been found that a polymer and modifier having solubility parameters of about 9.57 and about 14.39, respectively, are compatible. In this instance, the polymer is a 90/10 L-lactide/D,L-lactide copolymer and the modifier is N-ethyl o,p-toluene sulfonamide. Relevant polar characteristics, include hydrogen bonding index, dielectric constant, and dipole moment.

One measure of polar interaction between two materials is the hydrogen bonding index. This index is derived from the infrared spectral shifts of deuterated methanol when complexed with the substance under investigation. Preferably, the hydrogen bonding indices of the polymer and modifier are within less than about 10 units of each other, more preferably, less than about 5 units of each other and more preferably less than about 2 units of each other.

The dielectric constant of a substance refers to its ability to resist the transmission of an electrostatic force from one charged body to another. Preferably, the dielectric constants of the modifier and polymer, at 25° C., are within about 20 units of each other, more preferably within about 5 units of each other, and even more preferably within about 2 units of each other.

A further component of compatibility between the polymer and modifier is the relative dipole moments of the polymer and modifier. The term "dipole moment" refers generally to the polarity of molecules and, more particularly, is the distance between charges multiplied by the quantity of charge in the electrostatic portions of the molecule. Typically, the dipole moments of the polymer and modifier are within about 6 units of each other, more preferably within about 2 units of each other, and even more preferably within about 1 unit of each other.

Another aspect of compatibility is the similarity between the polymer and modifier in terms of hydrophilic lipophilic balance ("HLB"). HLB is a measure of a material's relative hydrophilic and lipophilic nature. HLB has scale of zero to 20 in which a fully hydrophilic material would be 20 and a saturated hydrocarbon would be zero. The HLB of compounds with both hydrophilic and lipophilic portions is determined by dividing the weight percent of the hydrophilic portion by 5.

The HLB value of polylactic acid is approximately 10 and that of polyglycolic acid is approximately 15. Lactide has an HLB of 12 and glycolide is 15. A typical good plasticizer for polylactic acid is dimethyl adipate (HLB=10). This plasticizer did not function with polyglycolic acid. A plasticizer that functioned marginally with polylactic acid was lauronitrile. It has an HLB of 3, but its hydrophilic group is extremely polar.

The HLB values of the plasticizer should be within about 4 units, and preferably within 2 units, of the polymer to be plasticized. Special circumstances can stretch the range to about 7 HLB units.

It has also been found that when polymers of the present invention are able to adopt varied three-dimensional configurations, the polymers are compatible with a wide variety of modifiers. For example, polymers which are less crystalline in nature are typically able to adopt more varied three-dimensional structures than polymers which are relatively crystalline. Copolymers are usually less crystalline in nature than homopolymers. As a specific example, a copolymer with monomeric units selected from L-lactide, D-lactide and glycolide is typically less crystalline than homopolymers of any of the three materials.

Typically, polymers which have less than about 20 percent crystallinity, more preferably less than about 10 percent crystallinity, and more preferably less than about 5 percent crystallinity have suitably varied three-dimensional configurations for advantageous compatibility characteristics. Crystallinity can be measured by various standard techniques. In addition, as noted above, the polymers of the present invention are preferably copolymers, more preferably copolymers in which no one monomer constitutes more than about 95 weight percent of the polymer, more preferably no one monomer constitutes more than about 85 weight percent of the polymer and more preferably no one monomer constitutes more than about 75 weight of the polymer.

Nontoxicity

The reference to the polymer and modifier of the present material being non-toxic refers to the materials being non-toxic subsequent to processing, during use and subsequent to discard into the environment, including the degradation products of the polymer being non-toxic. For example, a material such as glycerin, which is on the FDA generally regarded as safe (GRAS) list, can be used as a plasticizer, but under certain processing conditions can be converted to acrolein, which is a suspected carcinogen. Thus, the various materials of the present invention can be processed so that otherwise non-toxic materials are not converted to toxic materials.

As used herein, the term "nontoxic" generally refers to substances which, upon ingestion, inhalation, or absorption through the skin by a human or animal, do not cause, either acutely or chronically, damage to living tissue, impairment of the central nervous system, severe illness or death. The term "nontoxic" can also refer to compounds, the hydrolysate or metabolites of which can be incorporated innocuously and without harm to the ecosystem. Preferably, the nontoxic polymer and modifier of the present materials are generally regarded as safe (GRAS) as that term is used by the United States FDA, or any other similar classification which may be used in the future. The toxicity level, as indicated by the Hazardous Substance Data Base of the National Library of Medicine, is an important factor in determining the suitability of each polymer and modifier for each application.

Preferred nontoxic modifiers include modifiers selected from the group consisting of acetyl tributyl citrate, lactide, glycolide, lactic acid esters, dimethyl adipate, diethyl adipate, caprolactone, acetyl triethyl citrate, bis 2-ethyl hexyl sebacate, bis 2-ethyl hexyl adipate, dibutyl sebacate, and triethyl citrate. Even more preferred nontoxic modifiers of the present invention are selected from the group consisting of acetyl tributyl citrate, lactide, glycolide, lactic acid esters, dimethyl adipate, diethyl adipate, caprolactone, acetyl triethyl citrate, bis 2-ethyl hexyl sebacate and bis 2-hexyl adipate.

INTERNALLY MODIFIED POLYMER COMPOSITIONS

Polydioxaneones and Nitrogen Analogues

Materials of the present invention, which involve internally modified polymer compositions, comprise polymers, generally referred to herein as polydioxaneones, having first repeating units of the formula

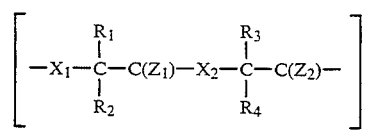

where, independently for each such first repeating unit: $X_1$ and $X_2$ are independently O or NR' and R' is independently H, hydrocarbyl, substituted hydrocarbyl or a hydrocarbyl derivative, including heteroatom containing constituents; $R_1$, $R_2$ and $Z_1$ combined have at most one carbon atom; $R_3$, $R_4$ and $Z_2$ combined have at most one carbon atom; and $Z_1$ and $Z_2$ are each independently one or more constituent group (e.g., hydrogen, hydrocarbyl, oxygen, etc.) extending from the polymer backbone chain and being covalently bonded to a tetravalent carbon atom in the polymer backbone chain, at least one of $Z_1$ and $Z_2$ being an oxygen that forms a carbonyl group with the associated carbon atom in the polymer backbone chain;

and having second repeating units of the formula

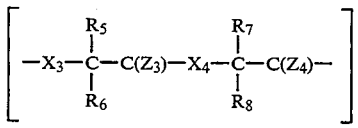

where, independently for each such second repeating unit: $X_3$ and $X_4$ are independently O or NR' and R' is independently H, hydrocarbyl, substituted hydrocarbyl or a hydrocarbyl derivative, including heteroatom containing constituents; $R_5$, $R_6$, $R_7$ and $R_8$ combined have at least four carbon atoms; and $Z_3$ and $Z_4$ are each independently one or more constituent group (e.g., hydrogen, hydrocarbyl, oxygen, etc.) extending from the polymer backbone chain and being covalently bonded to a tetravalent carbon atom in the polymer backbone chain, at least one of $Z_3$ and $Z_4$ being an oxygen that forms a carbonyl group with the associated carbon atom in the polymer backbone chain.

First and second repeating units can be present in the polymer in any fashion, including in random, alternating and block configurations. As used herein, hydrocarbyl refers to any constituent group having only hydrogen and carbon atoms, including aliphatic, aromatic, cyclic, noncyclic, saturated, and unsaturated constituents.

Polymers of the materials of the present invention are generally referred to herein as polydioxaneones. It will be recognized, however, that when any of $X_1$, $X_2$, $X_3$ or $X_4$ are NR, then the polymer may contain amide linkages characteristic of polyamino acids. As used herein, polydioxaneone generally refers to polymers having repeating units characteristic of monomers of dioxaneones, or the nitrogen-containing analogues thereof. Dioxaneone as used herein is in a general context to refer to a class of compounds having a dioxane ring, or a nitrogen-containing analogue ring thereof, and having one or more carbonyl oxygens pendant from that ring. Preferably, at least one of $X_1$ and $X_2$ and at least one of $X_3$ and $X_4$ is oxygen. When all of $X_1$, $X_2$, $Z_1$ and $Z_2$ are oxygen, the first repeating unit would be characteristic of a repeating unit derived from a dioxanedione monomer, a particular type of dioxaneone having two carbonyl groups. Likewise, when all of $X_3$, $X_4$, $Z_3$ and $Z_4$ are oxygen, the second repeating unit would be characteristic of polymerization of a dioxanedione. Specific examples of dioxanediones include, for example, lactide, glycolide and other cyclic diesters of $\alpha$-hydroxycarboxylic oxides. Polymers having repeating units characteristic of dioxanedione monomers can be referred to more specifically as polydioxanediones. As used herein, polydioxanedione includes nitrogen-containing analogues, having nitrogen rather than oxygen, as one or more of $X_1$, $X_2$, $X_3$ and $X_4$ in the polymer backbone. Likewise, as used herein, dioxanedione includes nitrogen analogues, such as, for example, dilactams.

In one embodiment, first repeating units have the formula

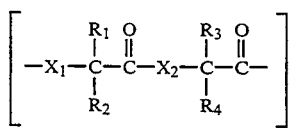

where, independently for each such first repeating unit: $X_1$ and $X_2$ are independently O or NR' and R' is independently H or hydrocarbyl; $R_1$ and $R_2$ combined have at most one carbon atom; and $R_3$ and $R_4$ combined have at most one carbon atom.

In one embodiment, second repeating units are of the formula:

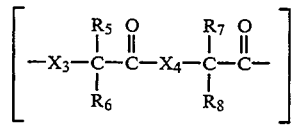

where, independently for each such second repeating unit: $X_3$ and $X_4$ are independently O or NR' and R' is independently H or hydrocarbyl; and $R_5$, $R_6$, $R_7$ and $R_8$ combined have at least four carbon atoms.

In one embodiment, the materials of the present invention comprise a polymer having one or more repeating units in addition to the first and second repeating units. For example, such additional repeating units could be derived from additional dioxaneone monomers or from other monomers capable of polymerization with dioxaneones, including lactones, such as $\beta$-butyrolactone, $\gamma$-butyrolactone, $\gamma$-valerolactone, $\delta$-valerolactone, $\epsilon$-caprolactone, lactams, epoxides, glycols, succinic acid, tartaric acid, mandelic acid, benzylic acid, and others. The polymers could, therefore, be copolymers containing in excess of two comonomers. Particularly preferred as additional repeating units are those representative of polymerization of glycols (also known as dihydric alcohols or diols). For example, blocks of such glycols could be added into a polymer having first and second repeating units by adding the glycols to a reactive bath following polymerization to form the first and second repeating units. Any glycol, such as ethylene or propylene glycol could be used.

The polymers may be plasticized using external plasticizers. In a preferred embodiment, however, the polymer is substantially free of any external plasticizer. Rather, the first repeating units and the second repeating units are selected to provide the desired physical properties, thereby eliminating the need for external plasticizers and associated costs and complexities of using the same. Not to be bound by theory, it is believed that second repeating units impart flexibility into the composition by breaking up the structural regularity otherwise imparted by the first repeating unit, thereby providing the possibility for an amorphous polymer with a substantial amount of internal freedom.

In one embodiment, first repeating units comprise greater than 50 weight percent of the polymer, preferably from about 50 weight percent to about 99 weight percent of the polymer, more preferably from about 80 weight percent to about 99 weight percent of the polymer still more preferably from about 90 weight percent to about 99 weight percent of the polymer, and most preferably from about 90 weight percent to about 97 weight percent of the polymer.

In one embodiment, the second repeating units comprise less than 50 weight percent of the polymer, preferably from about 1 weight percent to about 50 weight percent of the polymer, more preferably from about 1 weight percent to about 20 weight percent of the polymer, still more preferably from about 1 weight percent to about 10 weight percent of the polymer, and most preferably from about 3 weight percent to about 10 weight percent of the polymer.

In an embodiment the first reacting units have a molecular weight less than about 145. Such first repeating units could be derived, for example, from polymerization of lactide and/or glycolide monomers.

In one embodiment, second repeating units are derived from polymerization of tetramethyl glycolide. In another embodiment, second repeating units are derived from polymerization of the cyclic diester of α-hydroxyisovaleric acid. In another embodiment, second repeating units are derived from polymerization of the cyclic diester of α-hydroxycaproic acid. In another embodiment, second repeating units are derived from polymerization of the cyclic diester of α-hydroxyisocaproic acid. In yet another embodiment, the second repeating units are derived from polymerization of the cyclic diester of α-hydroxyoctanoic acid. It will be recognized by those skilled in the art that the hydrocarbyl side chain in the branched isomers of α-hydroxyisovaleric acid and α-hydroxyisocaproic acid could take one of multiple forms. In one embodiment, such branched isomers comprise a mixture of two or more of those possible for such an iso-acid compound.

In one particularly preferred embodiment, first repeating units are derived from polymerization of lactide and second repeating units are derived from monomers selected from the group consisting of tetramethyl glycolide, the cyclic diester of α-hydroxyisovaleric acid, the cyclic diester of α-hydroxycaproic acid, the cyclic diester of α-hydroxyisocaproic acid, the cyclic diester of α-hydroxyoctanoic acid, and combinations thereof.

The constituents $R_1$, $R_2$, $R_3$, $R_4$, $R_5$, $R_6$, $R_7$, and $R_8$ may be any organic constituents, but preferably are hydrocarbyl or hydrogen. $R'$ is preferably hydrogen or hydrocarbyl.

In one embodiment, at least one of $R_5$ and $R_6$ and at least one of $R_7$ and $R_8$ are hydrocarbyl radicals having from two to three carbon atoms. In another embodiment, at least one of $R_5$, $R_6$, $R_7$ and $R_8$ is a hydrocarbyl radical having from 4 carbon atoms to about 24 carbon atoms, preferably from 4 carbon atoms to about 16 carbon atoms, and more preferably from 4 carbon atoms to about 10 carbon atoms. In one preferred embodiment, the total number of carbon atoms in $R_5$, $R_6$, $R_7$, and $R_8$ combined is at least 5, and more preferably is from 5 to about 12. In one embodiment, at least one of $R_5$ and $R_6$ and at least one of $R_7$ and $R_8$ is a saturated hydrocarbyl radical. In a preferred embodiment, $R_5$, $R_6$, $R_7$ and $R_8$ are each independently either hydrogen or hydrocarbyl.

In one embodiment, one of $R_5$ and $R_6$ is isopropyl and the other is hydrogen, and one of $R_7$ and $R_8$ is isopropyl and the other is hydrogen. In another embodiment, one of $R_5$ and $R_6$ is propyl and the other is methyl, and one of $R_7$ and $R_8$ is propyl and the other is methyl.

In one embodiment, the constituents $R_5$ and $R_6$ are the same as the constituents $R_7$ and $R_8$, such as would be the case if the second repeating units were derived from a symmetrically substituted dioxanedione. In another embodiment, the total number of carbon atoms in $R_5$ and $R_6$ combined is different than the number of carbon atoms in $R_7$ and $R_8$ combined, such as would be the case if the second repeating units were derived from an unsymmetrically substituted dioxanedione.

In one embodiment, the polymers of the present invention have a weight-average molecular weight of greater than about 30,000, preferably greater than about 70,000 and more preferably greater than about 100,000. Although the desired weight-average molecular weight of the polymer will depend upon the specific product embodiment, as discussed below, one generally preferred range is a weight-average molecular of from about 100,000 to about 500,000, and more preferably from about 150,000 to about 250,000.

Monomers

Monomers useful for preparing first repeating units and second repeating units of polymers, from which materials of the present invention are made, can be any monomers that, when polymerized, result in the first and second repeating units respectively. Such monomers could be, for example, α-hydroxycarboxylic acids or esters, salts or amides thereof. Preferably, however, the monomers used to prepare the first repeating units and second repeating units are cyclic compounds, such as dioxaneones or nitrogen-containing analogues thereof. Preferably, first monomers result in first repeating units upon polymerization and second monomers result in second repeating units upon polymerization. In one embodiment, cyclic compounds used as monomers to prepare polymers of the present materials comprise first monomers of the formula

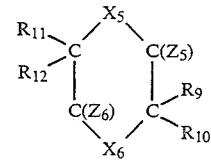

where, independently for each such first monomer: $X_5$ and $X_6$ are independently O or NR' and R' is independently H, hydrocarbyl, substituted hydrocarbyl or a hydrocarbyl derivative, including hetero-atom containing constituents; $R_9$, $R_{10}$ and $Z_5$ combined have at most one carbon atom; $R_{11}$, $R_{12}$ and $Z_6$ combined have at most one carbon atom; and $Z_5$ and $Z_6$ are each independently one or more constituent group (hydrogen, hydrocarbyl, oxygen, etc.) extending from the ring and being covalently bonded to a tetravalent carbon atom in the ring, at least one of $Z_5$ and $Z_6$ being an oxygen that forms a carbonyl group with the associated carbon atom in the ring;

and comprise second monomers of the formula

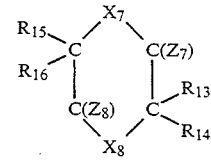

where, independently for each such second monomer: $X_7$ and $X_8$ are independently O or NR' and R' is independently H, hydrocarbyl, substituted hydrocarbyl or a hydrocarbyl derivative, including heteroatom containing constituents; $R_{13}$, $R_{14}$, $R_{15}$ and $R_{16}$ combined have at least four carbon atoms; and $Z_7$ and $Z_8$ are each independently one or more constituent group (hydrogen, hydrocarbyl, oxygen, etc.) extending from the ring and being covalently bonded to a tetravalent carbon atom in the ring, at least one of $Z_7$ and $Z_8$ being an oxygen that forms a carbonyl group with the associated carbon atom in the ring.

When both $Z_5$ and $Z_6$ are carbonyl oxygens, then the first monomers are dioxanediones, or nitrogen-containing analogues thereof. When both $Z_7$ and $Z_8$ are carbonyl oxygens, then the second monomers are dioxanediones, or nitrogen-containing analogues thereof. R' is preferably hydrogen or hydrocarbyl.

In one embodiment, first monomers are dioxanediones, or nitrogen-containing analogues thereof, of the formula

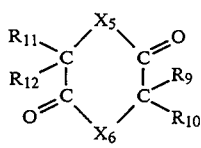

where, independently for each such first monomer: $X_5$ and $X_6$ are independently O or NR' and R' is independently H or hydrocarbyl; $R_9$ and $R_{10}$ combined have at most one carbon atom; and $R_{11}$ and $R_{12}$ combined have at most one carbon atom.

In one embodiment, second monomers comprise dioxanediones, or nitrogen-containing analogues thereof, of the formula

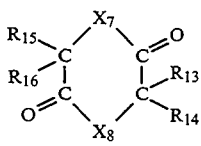

where, independently for each such second monomer: $X_7$ and $X_8$ are independently O or NR' and R' is independently H or hydrocarbyl; and $R_{13}$, $R_{14}$, $R_{15}$ and $R_{16}$ combined have at least four carbon atoms.

Preferably, at least one of $X_5$ and $X_6$ and at least one of $X_7$ and $X_8$ is oxygen. $R_9$, $R_{10}$, $R_{11}$, $R_{12}$, $R_{13}$, $R_{14}$, $R_{15}$ and $R_{16}$ can be the same or different from each other and can be any organic constituent such as hydrogen, hydrocarbyl, substituted hydrocarbyl, saturated hydrocarbyl, and others, including hetero-atom containing constituents. Preferably, $R_9$, $R_{10}$, $R_{11}$ and $R_{12}$ are hydrogen or hydrocarbyl, and if hydrocarbyl are more preferably saturated hydrocarbyl. $R_{13}$, $R_{14}$, $R_{15}$ or $R_{16}$ could be, for example, a furfural-based constituent, a vinyl-based constituent, a constituent having an aromatic ring. $R_{13}$ and $R_{14}$ or $R_{15}$ and $R_{16}$, respectively, could connect to form a single constituent, such as a cyclic constituent in which the ring of the constituent includes a carbon atom of the dioxane ring, such as in a spiro compound, such as, for example:

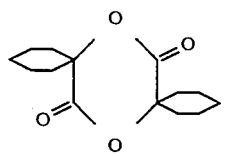

Preferably, however, $R_{13}$, $R_{14}$, $R_{15}$ and $R_{16}$ are hydrogen or hydrocarbyl, and if hydrocarbyl are more preferably saturated hydrocarbyl.

In one embodiment, first monomers have a molecular weight less than about 145. Such first monomers could be, for example, lactide, and/or glycolide.

In one embodiment, second monomers comprise tetramethyl glycolide. In another embodiment, second monomers comprise the cyclic diester of α-hydroxyisovaleric acid. In another embodiment, second monomers comprise the cyclic diesters of α-hydroxycaproic acid. In another embodiment, second monomers comprise the cyclic diester of α-hydroxyisocaproic acid. In another embodiment, second monomers comprise the cyclic diester of α-hydroxyoctanoic acid.

In one embodiment, at least one of $R_{13}$ and $R_{14}$ and at least one of $R_{15}$ and $R_{16}$ are hydrocarbyl radicals having from two to three carbon atoms. In another embodiment, at least one of $R_{13}$, $R_{14}$, $R_{15}$ and $R_{16}$ is a radical having from 4 carbon atoms to about 24 carbon atoms, preferably from about 4 carbon atoms to about 16 carbon atoms, and more preferably from about 4 carbon atoms to about 10 carbon atoms. In one preferred embodiment, the total number of carbon atoms in $R_{13}$, $R_{14}$, $R_{15}$ and $R_{16}$ combined is at least 5 and more preferably from 5 to about 12. In one embodiment, at least one of $R_{13}$ and $R_{14}$ and at least one of $R_{15}$ and $R_{16}$ are saturated hydrocarbyl radicals.

In one embodiment, one of $R_{13}$ and $R_{14}$ is isopropyl and the other is hydrogen, and one of $R_{15}$ and $R_{16}$ is isopropyl and the other is hydrogen. In another embodiment, one of $R_{13}$ and $R_{14}$ is propyl and the other is methyl, and one of $R_{15}$ and $R_{16}$ is propyl and the other is methyl.

In one embodiment, the constituents $R_{13}$ and $R_{14}$ are the same as the constituents $R_{15}$ and $R_{16}$, such as would be the case, for example, for a symmetrically substituted dioxanedione. In another embodiment, the total number of carbon atoms in $R_{13}$ and $R_{14}$ combined is different than the number of carbon atoms in $R_{15}$ and $R_{16}$ combined, such as would be the case, for example, for an unsymmetrically substituted dioxanedione.

In one embodiment, first monomers comprise from about 50 weight percent to about 99 weight percent of the total monomers from which the polymer is prepared, such as, for example, in a monomer mixture comprising both first monomers and second monomers. Preferably, first monomers comprise from about 80 weight percent to about 99 weight percent of the total monomers, more preferably from about 90 weight percent to about 99 weight percent of the total monomers, and most preferably from about 90 weight percent to about 97 weight percent of total monomers.

In one embodiment, second monomers comprise from about 1 weight percent to about 50 weight percent of the total monomers from which the polymer is prepared. Preferably, second monomers comprise from about 1 weight percent to about 20 weight percent of the total monomers, more preferably from about 1 weight percent to about 10 weight percent of the total monomers, and most preferably from about 3 weight percent to about 10 weight percent.

Preparation of Monomers

Cyclic compounds that may be used as monomers for manufacturing the polymers of the present materials can be prepared using any suitable method. Dioxanedione monomers, or nitrogen-containing analogues thereof, are preferably prepared directly from noncyclic α-hydroxycarboxylic acid esters or nitrogen-containing analogues, such as α-hydroxyamides, or from derivatives, such as salts, of either, thereby avoiding problems inherent with conventional backbiting methods. Such esters, amides and derivatives thereof can be prepared from base molecules, such as for example, α-hydroxycarboxylic acids and/or α-hydroxyamides. A more detailed discussion of methods useful for producing cyclic compounds, such as dioxaneones, and particularly dioxanediones, or nitrogen-containing analogues thereof, directly from noncyclic esters, or nitrogen-containing analogues such as amides, is provided in co-pending, commonly assigned U.S. application Ser. No. 07/854,559 for "Method to Produce Cyclic Esters", by Benecke et al., filed Mar. 19, 1992, and U.S. application Ser. No. 08/127,797 now U.S. Pat. No. 5,420,304 for "Method to Produce Cyclic Esters", by Verser et al., filed on even date herewith, both of which are incorporated herein in their entireties.

To better describe the production of cyclic compounds such as dioxanediones, or nitrogen-containing analogues thereof, directly from the noncyclic ester species, the following nomenclature, as more fully explained in U.S. application Ser. No. 07/854,559, may be used. Base molecules, such as α-hydroxycarboxylic acids, α-hydroxyamides, and salts and other derivative compounds (e.g., esters, ethers and salts with other than base molecules) of the foregoing are referred to as $Y_1A$. $Y_2A$ refers to a noncyclic, linear dimer, such as, for example, a molecule formed by a single reaction between any two $Y_1A$ molecules to form a noncyclic, straight chain, dimer having an ester or amide linkage. For example, the molecule formed by a single esterification of two α-hydroxycarboxylic acid base molecules would be a $Y_2A$. A $Y_3A$ refers to a noncyclic, linear trimer of base molecules having ester and/or amide linkages. $Y_4A$ refers to a noncyclic, linear tetramer having ester and/or amide linkages and $Y_nA$ refers to a noncyclic, linear n-mer. It should be recognized that $Y_2A$ is not limited by its method of formation, and could, for example, be formed by depolymerization, or by another decomposition reaction, of a larger oligomeric molecule, such as from a $Y_3A$ or a $Y_4A$ or a larger $Y_nA$. Likewise, any $Y_nA$ could be a depolymerization product of a larger oligomer. As used herein, YA without subscript generally denotes at least one of and generally a mixture of two or more of $Y_1A$, $Y_2A$, $Y_3A$, and $Y_4A$, or a solution thereof. When Y is substituted by L or G, specific corresponding compounds based on lactic acid and glycolic acid, respectively, are meant. For example, LA refers to $L_1A$, $L_2A$, $L_3A$, $L_4A$, etc. YD refers generically to a dioxanedione, or a nitrogen-containing analog thereof. LD refers specifically to lactide. As used herein, an amide refers to molecules that have an acyl group, being the nitrogen-containing analogue of a carboxyl group such as would be the case for a nitrogen-containing analogue of a carboxylic acid, and also molecules that have an amide linkage, such as would be the case for a nitrogen-containing analogue of an ester linkage.

A cyclic compound of dioxanedione, or a nitrogen-containing analogue thereof, derived from $Y_1A$ is produced by providing a compound mixture containing components including but not limited to YA, and treating the feedstream to form cyclic compounds which may be used as monomers for polymers of the present materials, as previously described. Not to be bound by theory, it is believed that the cyclic ester, or nitrogen-containing analogue, is formed primarily directly from a linear dimer, i.e., from $Y_2A$. Under certain reaction conditions, however, it is believed that $Y_3A$ and $Y_4A$ also contribute to dioxanedione formation. As used herein, forming the dioxanedione primarily directly from $Y_2A$ refers to a reaction in which $Y_2A$, such as $Y_2A$ already present in the feedstream or $Y_2A$ formed by an esterification reaction between two $Y_1A$ molecules, is converted to a cyclic compound of dioxanedione or a nitrogen-containing analogue thereof by ring-closing esterification or by a ring-closing formation of an internal amide linkage. That is, the cyclic compound is not formed by backbiting of polyester chains, as described in the prior art when a dioxanedione is formed from $Y_5A$ or greater.

In one embodiment, cyclic esters or nitrogen-containing analogues thereof such as amides, including dioxanediones, are prepared from a noncyclic ester or nitrogen-containing analogue thereof, by treatment including removal of water from a compound mixture including reactive components and an organic or silicon-based solvent.

In this embodiment, water initially in the compound mixture is removed rapidly leading to an essentially dehydrated feedstream having a water concentration of less than about 2 wt %. Water formed by the esterification reactions is preferably removed essentially as it is formed. In particular, water is typically removed at a rate such that the concentration of water in the treated compound mixture is less than about 2 wt %, more preferably less than about 1 wt %, and even more preferably less than about 0.5 wt %.

Water can be removed from a compound mixture by a variety of methods, including, but not limited to: evaporation; a solvent-based reaction process, such as a reactive distillation process; removal of water as an azeotrope from a feedstream in which the reactive components are diluted in a solvent which forms an azeotrope with water; adding a water-getter which preferentially reacts with water; using molecular sieves or partitioning (e.g., osmotic) membranes; using anhydrous salts that form hydrated crystals with water; contacting the feedstream with water absorptive materials, such as polysaccharides or silica.

As noted above, the reaction is preferably conducted in a solvent. Preferably, the reactive components of the compound mixture are present in dilute concentration in a solvent. For example, the concentration of YA can be less than about 25% by weight of a feedstream. Preferably, YA species are 100% soluble in the solvent at reaction conditions.

Preferably, the solvent is relatively polar because it is believed that more polar solvents, such as anisole, favor the selective formation of YD over $Y_5A$ and higher oligomers. Suitable solvents for use in the present invention can include aromatic solvents, aliphatic solvents, ethers, ketones, silicon-based solvents and halogenated solvents. Preferred solvents are aromatic solvents.

Specific solvents of the present invention include 2-butanone, 2-heptanone, 2-hexanone, 2-pentanone, acetone, anisole, butyl ether, ethyl ether, isopropyl ether, methyl-phenyl ether, benzene, cumene, m-xylene, o-xylene, p-xylene, toluene, cyclohexane, heptane, hexane, nonane, octane, 1-pentene, 2-octanone, dimethyl sulfoxide, phenetole, 4-methyl anisole, 1,3-dimethoxybenzene, 1,2-dimethoxybenzene, 1,4-dimethoxybenzene, mesitylene, chlorobenzene, 1,2-dichlorobenzene, 1,3-dichlorobenzene, 1,4-dichlorobenzene, 2-chlorotoluene, 4-chlorotoluene, veratrole, and 3-chlorotoluene. Preferred solvents include toluene, xylene, anisole, phenetole, 4-methyl anisole, 1,3-dimethoxy benzene, and mesitylene. Particularly preferred solvents of the present invention include xylene, anisole and 4-methyl anisole.

Substituted aromatic solvents are particularly preferred for the present invention. Such solvents are typically polar and thus, provide high selectivity. Also preferred are di-substituted aromatics, such as 4-methyl anisole.

The cyclic compound formed by the above-described process can be recovered and purified, for example, by crystallization, solvent extraction, distillation, membrane partitioning, washing with solvent, chromatography, sublimation, and combinations thereof. Preferably, the cyclic compound is a dioxanedione, or a nitrogen-containing analogue thereof, all as previously described.

The role played by water in the present process can be appreciated by reference to the following equilibrium reactions:

$$2Y_1A \rightleftharpoons Y_2A + H_2O,$$

$$Y_2A \rightleftharpoons YD + H_2O,$$

$$Y_1A + Y_2A \rightleftharpoons Y_3A + H_2O,$$

etc. Thus, it will be observed that $Y_1A$ is in equilibrium with higher oligomers of $Y_1A$, cyclic esters and water. By removing water, the reactions are driven to the right and, conversely, by adding water the reactions are driven to the left.

Different monomers useful in preparing polymers for the present materials, as previously discussed, can be prepared individually and mixed together for polymerization, or they can be prepared together. When prepared individually, for example, a first monomer could be prepared from first YA species (e.g., from a first $Y_2A$). A second, different monomer could be separately prepared from second YA species (e.g., from a second $Y_2A$). The first and second monomers, preferably following purification of each, could then be mixed together and copolymerized to form a polydioxaneone useful in making the materials of the present invention.

In another embodiment, a first monomer and a second monomer could both be prepared from a single feed. The feed could contain, for example, two different base molecule species, preferably with one present in a much lower concentration than the other. In such a feed mixture, the $Y_2A$ would comprise first linear dimers representative of two first base molecules and would also comprise second two linear dimers representative of one of a first base molecule and one of a second base molecule. If the concentration of first base molecules is sufficiently high compared to second base molecules, then the feed would not comprise appreciable amounts of $Y_2A$ other than the two already described. The monomers produced would then comprise primarily first monomers that are symmetrically substituted dioxanediones, or nitrogen-containing analogues thereof, being the cyclic compounds representative of two of the first base molecule. The monomers produced would also comprise a smaller amount of second monomers that are unsymmetrically substituted dioxanediones, or nitrogen-containing analogues thereof, being the cyclic compounds representative of one of a first base molecule and one of a second base molecule. For example, lactic acid (i.e., α-hydroxypropanoic acid) and α-hydroxyoctanoic acid could be mixed as first and second base molecules in a feed. First monomers would then be a cyclic diester representative of two lactic acids (i.e., lactide) and second monomers would then be a cyclic diester representative of one lactic acid and one α-hydroxyoctanoic acid. This process could also be used to make more than two different dioxanedione monomers together.

Additional information relating to internally modified polymer compositions can be found in co-pending, commonly assigned U.S. patent application Ser. No. 08/127,907 for "DEGRADABLE POLYDIOXANE-ONE-BASED MATERIALS," by Lipinsky et al., filed on even date herewith, which is incorporated by reference herein in its entirety.

PREPARATION OF POLYMERS

The polymer of the present materials can be prepared by a variety of polymerization techniques. The polymerization reaction is conducted in the liquid phase in a closed, evacuated vessel. Alternatively, the polymer can be prepared at atmospheric pressure with the polymerization mixture blanketed by an inert gas such as, for example, nitrogen. If the polymerization reaction is conducted in the presence of oxygen or water, such as would be the case for air, some discoloration or chain termination or catalyst deactivation can occur in the final polymer with a resulting decrease in molecular weight and tensile strength.

Typically, the polymerization is conducted above the melting point of the monomers and below a temperature at which degradation of the resulting polymer occurs. The catalysts used in the polymerization reaction of the present invention can be metal salts and esters of carboxylic acids containing up to 18 carbon atoms. Examples of such acids are formic, acetic, propionic, lactic, butyric, valeric, caproic, 2-ethylhexanoic, caprylic, pelargonic, capric, lauric, myristic, palmitic, stearic, and benzylic acids. For example, good results can be obtained in the polymerization of lactide using stannous acetate or stannous caprylate.

The catalyst is used in normal catalytic amounts for polymerization. For example, a stannous 2-ethylhexanoate catalyst concentration in a range of about 0.001 to about 2 percent by weight, based on total weight of the monomers or comonomers, is suitable for polymerization of lactide. A catalyst concentration in the range of about 0.01 to about 1.0 percent by weight is preferred. Particularly preferred is a catalyst concentration in the range of about 0.02 to about 0.5 percent by weight. The exact amount of catalyst in any particular case depends to a large extent upon the catalyst employed and the operating variables, including time, temperature and the desired rate of reaction.

The reaction time of the polymerization process is dependent on various reaction variables, including reaction temperature, polymerization catalyst, amount of catalyst, degree of mixing, and whether a solvent is used. The reaction time can vary from a matter of minutes to a period of hours or days, depending upon the particular set of conditions which is employed. Heating of the mixtures of monomers or comonomers is continued until the desired level of polymerization is attained. For example, the extent of polymerization can be determined by analysis for residual monomers. In general, it is preferred to conduct the polymerization in the absence of impurities which contain active hydrogen since the presence of such impurities tends to deactivate the catalyst and/or increase the reaction time. It is also preferred to conduct the polymerization under substantially anhydrous conditions.

The polymer of the present invention can be prepared by bulk polymerization, suspension polymerization or solution polymerization. The polymerization can be carried out in the presence of an inert normally-liquid organic vehicle such as, for example, aromatic hydrocarbons such as benzene, toluene, xylene, ethylbenzene and the like; oxygenated organic compounds such as anisole, dimethyl and diethyl ethers of ethylene glycol; normally-liquid saturated hydrocarbons including open chain, cyclic and alkyl-substituted cyclic saturated hydrocarbons such as hexane, heptane, cyclohexane, decahydronaphthalene and the like.

The polymerization process can be conducted in a batch, semi-continuous, or continuous manner. In preparing the monomeric reactants and catalysts for subsequent polymerization, they can be admixed in any order according to known polymerization techniques. Thus, the catalyst can be added to one comonomeric reactant. Thereafter, the catalyst-containing comonomer can be admixed with another comonomer. In the alternative, comonomeric reactants can be admixed with each other. The catalyst can then be added to the reactant mixture. If desired, the catalyst can be dissolved or suspended in an inert, normally-liquid organic vehicle. If desired, the monomeric reactants either as a solution or a suspension in an inert organic vehicle can be added to the catalyst, catalyst solution or catalyst suspension. Alternatively, the catalyst and comonomeric reactants can be added to a reaction vessel simultaneously. The reaction vessel can be equipped with a conventional heat exchanger and/or mixing device. The reaction vessel can be any equipment normally employed in the art of making polymers. One suitable vessel, for example, is a stainless steel vessel.

MATERIAL TYPES

As discussed above, the present invention is directed to a variety of products made of degradable materials. The degradable materials include the polymer and modifier. The various materials of the present invention have varying chemical and physical characteristics which are relevant to their intended uses. The materials of the present invention include the following types: films, fibers, molded products, laminates, foams, powders, nonwovens, adhesives, coatings, extruded profiles, beads, and colorant carriers.

Film material of the present invention is made from compositions as described above. The term film, as used herein, refers to a material type which is a film in its final product configuration and does not refer to intermediate source materials which are subsequently processed into non-film products. The term film includes material commonly identified as a film with thicknesses of less than about 20 mil and also is intended to include materials which may also be termed sheets, including materials with thicknesses up to about 50 mil. Such films can be prepared to simulate the properties of common materials, such as polyethylenes, polystyrenes, and vinyls. The desired molecular weight and distribution for each application is achieved by adjustment of the polymerization conditions and by post-polymerization processing. Choices and percentages of modifier(s) affect flexibility and processing temperatures as well as the degradation rate. Such films can be produced by a variety of known processes. For example, films can be prepared by compression molding processes. Suitable films can also be prepared by extrusion processes, including blown film processes and by casting solutions of the polymer composition and then recovering the solvent. Thermal annealing and quenching are two methods that control the morphology of the film to emphasize selected properties. Quenching as used herein indicates that the temperature of a material is dropped rapidly to prevent extensive crystallization of the polymer. Crystallization of polymers is a slow process, requiring minutes to hours to fully accomplish. When crystallization is desired, the temperature is held above the glass-transition temperature, $T_9$, for some time to allow the molecules to order themselves into extensive crystalline lattices. This process is called annealing. When cooled rapidly from an amorphous melt, the polymer does not have the time required for crystallization and remains largely amorphous. The time required to quench depends on the thickness of the sample, its molecular weight, melt viscosity, compositions, and its $T_9$. Note that melt viscosity and $T_9$ are lowered by plasticization which facilitates quenching. Thin films obviously cool very quickly because of their high surface-to-volume ratio while thicker films cool more slowly with their greater thicknesses. Regular structures such as homopolymers order more easily and crystallize more quickly than more random structures such as a copolymer.

Quenching to an amorphous state requires that the polymer or copolymer in an amorphous melt is rapidly cooled from its molten state to a temperature below its $T_9$. Failure to cool rapidly allows spherulitic crystallinity to develop, that is, crystalline domains of submicron to micron size. The latter scatters light and the polymer specimens become opaque. These crystalline forms have improved stability to heat distortion. This spherulitic crystallinity is often called short range order long-range disorder since the crystallites are separated by amorphous regions. However, the crystallites act as pseudo crosslinks to maintain dimensional stability above the $T_9$ but below their melting points. Alternatively stability to heat distortion can be obtained by orienting a crystallizable amorphous polymer. Here, the polymer molecules are stretched to allow some long-range ordering, then "heat set" to permit the ordering to complete, that is, given some time to anneal. The amorphous polymer is thereby crystallized into a different order, called long-range order, short-range disorder. Transparency and resistance to heat distortion are favored using this type of order.

Films of the present invention can be oriented or not and can be shrinkable or not. Orientation refers to stretching a film in at least one direction which allows for alignment and ordering of the polymer molecules along the direction of stretching. The stretching can be 2, 3 or 4 times the original length of film in the direction of stretching. Orienting can be uniaxial, which is typically in the direction the film travels as it is processed. Alternately, orienting can be biaxial which is typically in the direction the film travels as it is processed and in a second direction transverse to the first. Orientation is conducted at a film temperature above the $T_9$ of the film and below its melting point. Biaxially oriented films are useful as shrinkable films in shrink wrap packaging.

Biaxially oriented films can be dimensionally stabilized to heat by annealing under restraint after drawing at a temperature above the $T_9$ and below the melting point. This procedure allows internal tension in the film to relax and upon cooling the film is non-shrinkable.

As noted above, films of the present invention can be prepared having a variety of product characteristics. Such films can have polystyrene-like properties, low density polyethylene-like properties, high density polyethylene-like properties, polypropylene-like properties and polyvinyl chloride-like properties. Polystyrene-like films of the present invention typically have a weight average molecular weight between about 100,000 and 500,000, a $T_g$ of between about 100° C. and 105° C. when not oriented and a formstability to heat when oriented at between about 70° C. to about 150° C. a tensile strength of between about 6,000 psi and about 8,000 psi when not oriented, which approximately doubles when oriented 3× to 5×, a Shore D hardness of between about 80 and about 90, an elongation to break of about 2% to about 4% when not oriented, or 4% to 40% when oriented, an elastic modulus of greater than about 250,000 psi, and typically are transparent and are semicrystalline and degrade under ambient conditions in about 6 to about 24 months. Low density polyethylene-like film materials of the present invention typically have a weight average molecular weight from about 100,000 to about 500,000, a $T_g$ of about −20° C., a tensile strength of between about 1,500 psi and about 3,000 psi, a Shore D hardness of about 50, an elongation to break to about 150% to about 1,200%, an elastic modulus of between about 10,000 psi and about 50,000 psi, and is sometimes transparent, is not crystalline, and is degradable under ambient conditions in about 3 to about 12 months. High density polyethylene-like materials of the present invention typically have a weight average molecular weight of between about 100,000 and about 500,000, a $T_g$ of about room temperature to about −120° C., a tensile strength of between about 2,500 psi to about 4,000 psi, a Shore D hardness of between about 50 and about 60, an elongation to break of between about 50% and about 500%, an elastic modulus of between about 50,000 psi and about 125,000 psi, and is sometimes transparent, is crystalline, and is degradable under ambient conditions in from about 6 to about 24 months. Polypropylene-like films of the present invention typically have a weight average molecular weight of between about 100,000 and about 500,000, a Tg of about 0° C., a tensile strength of between about 4,000 and about 6,000, a Shore D hardness of about 70, an elongation to break of between about 100% and about 600%, an elastic modulus of between about 125,000 psi and about 200,000 psi, and is sometimes transparent, is crystalline, and is degradable under ambient conditions in from about 6 months to about 24 months. Polyvinyl chloride-like films of the present invention typically have a weight average molecular weight of between about 100,000 and about 500,000, a $T_g$ of below room temperature, a tensile strength of between about 300 psi and about 500 psi, a Shore D hardness of between about 10 and about 90, an elongation to break of between about 5% and about 500%, an elastic modulus of between about 500 psi and about 250,000 psi, and is sometimes transparent, is not crystalline, and is degradable under ambient conditions in from about 6 months to about 24 months.

A fiber-type material of the present invention is prepared by extruding a thin filament through a spinneret, and allowing the filament to cool prior to being rolled onto a spool. In this manner, the filament is maintained as a fiber. Polymers used for fibers are generally classified into two types, textile fibers used for products such as clothing, fabrics, carpets, draperies and industrial fibers used for products such as tire cords, reinforcements for composite applications, industrial use fabrics (e.g., sails, nets, ropes and tarps). Fibers used in textiles should be either dyeable or able to be colored in the melt by pigments. Moisture absorbances can range from about 0% to about 20% for most textile fibers. The polymers used in textile fibers should be resistant to the acidic or basic conditions encountered in dying, scouring (a type of laundering process) and finishing by applying, for example, soil resistance, antistatics and permanent press.

Typical textile fibers have breaking strengths from about 14 KPSI to about 87 KPSI and breaking elongations from between about 5% to about 60%. Industrial fibers generally have significantly higher breaking strengths of from about 100 KPSI to about 500 KPSI, have higher stiffness (modulus) and lower breaking elongations from about 1% to about 30%. Polymer molecular weight distributions for fiber grade polymers are generally narrow from about 2 to about 5 and weight average molecular weights from about 30,000Mw for condensation type polymers (e.g., nylons and terephthalate based polyesters) to about 150,000 MW for chain type polymers (e.g., polyolefins).

Molded product material of the present invention is made from compositions as described above. Molded product material can be made by a variety of processes, including blow molding, injection molding, open pot molding, and thermoforming. Blow molding is employed to make hollow shapes, especially packaging containers. In an extrusion embodiment of this process, a parison is made first and then expanded to the walls of the mold cavity. The degradable polymer composition is tailored to meet extrusion blow molding processing requirements by adjustment of comonomer ratio, molecular weight of the polymer product, and choice/percentage of modifier. These processing requirements are reconciled with the end use requirements with regard to shelf life, strength, speed of onset of degradation, and other parameters. Molecular weights of over 100,000 and as high as 500,000 are desirable for these applications. There are trade-offs in molecular weight and percent modifier such that flexible bottles can be made by use of polymeric plasticizers with moderate molecular weight degradable polymers. Polymeric plasticizers are not extracted into the liquid contents of containers, and the flexibility of the package renders it more impact-resistant.

Injection molding of thermoplastics is accomplished by melting the thermoplastic composition and transferring it into a closed mold cavity where it solidifies to conform to the shape of the mold. Injection molded products require little or no mechanical work before they are fabricated with other parts into an end use product.

The materials of this invention are highly suitable for injection molding because their melting points and morphology can be tailored in many different ways. Thus, a dense polymer (specific gravity=1.25) can be blended with less dense plasticizers that can fine-tune the consistency of the material to be injected. The molecular weights and distribution of molecular weight can be adjusted. Because the economics of injection molding usually necessitates short cycle times, relatively low molecular weights (less than 120,000) are desirable.

Injection molded products of the present invention typically have a weight average molecular weight of between about 50,000 and about 150,000 a $T_g$ of greater than about 50° C. a tensile strength of greater than about 3,000 psi, a Shore D hardness of between about 50 and about 90, an elongation to break of between about 2% and about 25%, an elastic modulus of between about 100,000 psi and about 400,000 psi, and are sometimes transparent, are semicrystalline, and degradable under ambient conditions in from about 6 months to about 24 months.

Similar to injection molding, open pot molding is accomplished by melting the thermoplastic composition and transferring it into an open mold where it solidifies to conform to the shape of the mold.

Thermoforming is a branch of molding that uses thick films or sheets of thermoplastic. Because the materials of this invention are especially easy to convert to film or sheet form that have excellent transparency, they are excellent candidates for thermoforming. The sheet must be heated to the point that it is quite flexible and then subjected to vacuum or pressure that presses the sheet against a mold, forming the desired shape. The plastic memory of these polymer-plasticizer combinations is a useful attribute in drape forming embodiments of thermoforming.

Another material type of the present invention includes laminates and coextrudates. Film laminates and coextruded films are composite materials in which each layer provides functional utility that complements the rest of the structure. The polymer/modifier materials of this invention provide degradability, in addition to such functions as strength, printability, and high transparency. The other layers in the laminate or coextruded structure can provide temporary protection against moisture or abrasion so that the onset of degradation is delayed until after the shelf-life and consumer-use phases have passed. The other layers may provide essential electrical or other functions that force the layer to be nondegradable; however, the adverse environmental impact can be reduced by using the polymers of this invention for most of the weight of the product.

Laminated or coextruded products of the present invention can be used in a variety of functions. For example, many packaging materials can be prepared from laminates or coextrudates. Such packaging materials, for example, have layers which perform various functions, such as structural stability, gas permeability, decoration and moisture exclusion. The polymer compositions of the present invention, can be used, for example, as a transparent outer protective coating for such a laminate product.

A laminate or coextrudate of the present invention typically has a weight average molecular weight of between about 50,000 and 500,000, a $T_g$ below about room temperature, a Shore D hardness of about 20 to about 70, an elongation to break of greater than about 300%, a tensile strength of between about 2,000 psi and about 40,000 psi, an elastic modulus of between about 20,000 and about 700,000 psi, and is not crystalline, and is degradable under ambient conditions in from about 1 month to about 2 years.

A further material type of the present invention includes foams. Foamed thermoplastics have large markets in food packaging. The materials of this invention are outstanding candidates for use in these applications because they can be melted to a high-viscosity material that can be blended with such gases as carbon dioxide or nitrogen for foam extrusion. The viscosity of the melt can be optimized by molecular weight and by modifier content. Typically, the polymer will have a molecular weight of more than 150,000 for foam extrusion. Polymeric modifiers are especially desirable for this foam application because a rather stiff bubble is desirable. The solubility (under pressure) of carbon dioxide in the polymers of this invention can be exploited to control pore size of bubbles that are produced after cooling.

Foam materials of the present invention typically have a weight average molecular weight of between about 50,000 and about 500,000, a $T_g$ of greater than 50° C., and are semicrystalline and are degradable under ambient conditions in between about 6 months to about 24 months.

A further material of the present invention includes spun-bonded nonwoven material. The term "spun-bonded nonwoven" refers to material which is prepared by extruding a thin film filament through a spinneret onto a flat cooled surface in an irregular pattern to form a relatively uniform sheet which is not in a woven pattern. Spunbonding requires adherence to a limited range of melt viscosities so that the roving spinnerets can deliver the appropriate amount of material to the cooled surface. The detailed response of the polymer melt to the quenching is also a sensitive processing parameter. Such nonwoven materials typically have high strength characteristics and can be used for envelopes and other similar containers. The polymers of this invention can be optimized to meet the processing requirements by manipulation of many variables, including control of molecular weight and molecular weight distribution and selection of comonomers. Typically, nonwoven material has a high molecular weight and have high elongation. Thus, the fibers are flexible and easily entangled. The nonwoven material can be hard or soft, absorbent or chemically resistant, depending upon the application. Modifiers play an important role by facilitating the initial bonding among fibers.

Polymers for spunbonded nonwovens are generally fiber grade type polymers, since the initial forming process has aspects of fiber spinning. Spinning speeds for the spunbonded filaments is in the 3,000 to 6,000 mole per minute range. The polymers should have sufficient thermal stability for steam or heat point bonding. The fabrics, particularly those used in disposable medical or clean room type uses, should be stable to sterilization by, for example, heat or chemical means, such as ethylene oxide. The fabrics also should not have or form lint and should resist fluid and bacterial penetration.

Spunbonded nonwovens generally have base weights of between about 0.8 ounces per square yard to about 5 ounces per square yard. Tensile strengths of the spunbonded nonwoven fabrics range from about 1 pounds to about 150 pounds in the machine or extrusion/fabric laydown direction (MD) and about 1.1 pounds to about 170 pounds in the transverse or cross direction (XD). Tear strengths range from about 1 pound to about 80 pounds in the MD and XD directions. Burst strengths (Mullen) range from about 35 KPSI to about 225 KPSI for spunbonded nonwoven fabrics.

A further product type of the present invention includes adhesives. The polymer compositions of this invention have considerable utility as adhesives because they can be hot-melt or solvent-based products. Choice of comonomers and the molecular weight distribution can affect the melting point of the hot melt and its changes in morphology during tackifying and hardening. The modifiers provide additional dimensions to the hot melt formulations. In addition to optimizing viscosity, the modifiers can act as a trigger to initiate a gradual degradation process. The solvents to be used in the solvent-based adhesives could be the modifier part of the formulation. The biocompatible modifiers of this invention (e.g., acetyl triethyl citrate or lactide) can provide the functions that some solvent based formulations obtained from toxic or flammable solvents.

The polymers of this invention that are to be used in adhesives range widely in composition and molecular weight, depending on the specific type of adhesive and the specific application. The surface properties of the substrates to be bonded are of great importance in the choice of polymer. For example, a polylactide ($M_w$ of about 200,000) was dissolved in a low boiling solvent and employed to bond together two pieces of wood. A strong bond was formed that lasted for more than two years at ambient temperatures in an office environment. Other substrates such as paper may need only $M_w$ of 10,000 to attain a strong bond. The excellent compatibility of polylactides and other polymers of this invention with substances with solubility parameters that differ widely among themselves indicates that these polymers are especially suited to bonding together disparate materials.

Adhesives of the present invention typically have a weight average molecular weight of between about 5,000 to about 200,000, a $T_g$ of less than room temperature, a Shore D hardness of about 0.5, an elongation to break of greater than about 300%, an elastic modulus of less than about 1,000, and are not transparent and are not crystalline.

A further material type of the present invention include various coatings. Unlike some films, moldings, and foams, coatings do not have to be strong enough to be self-supporting. Therefore, an extremely wide range of the polymer composition of this invention can be employed for coating use. The degradability aspect allows the coating to be a temporary protection of the underlying substrate against abrasion or other harm. The coating can serve many of the functions of a film, in particular, the coating may serve as a temporary printing surface so that the label of a container is among the first parts of a package to degrade.

The coating can serve as a binder to incorporate pigments onto writing papers. This type of usage can facilitate the degradation of the paper substrate by providing an acid environment for cellulose hydrolysis.

Generally, the polymers to be used on coatings can have a lower molecular weight and less crystallinity than those that are to be used in films. Thus, molecular weights may range from 10,000 to 100,000. However, in special circumstances, a combination of high molecular weight with a plasticizer can impart extra strength.

Another material type is an extruded profile material made from the above described compositions. The term extruded profile, as used herein, refers to a material type which is produced by a polymer composition being forced through a die of a particular shape so that the resulting material has a cross-sectional profile of that shape. The physical and chemical properties vary with the application. For example, polymers used in extruded profiles have a wide range of properties. The properties can range from soft medical tubes having strengths between 1,000 and 3,000 psi, moduli as low as 1,000 psi, and elongations to break up to 2,000% to very rigid structures having strengths as high as 12,000 psi, moduli as high as 600,000 psi, and elongation to breaks as low as 2%. Extruded products typically have good resistance to chemicals.

Molecular weights of extruded profile materials (extrusion or pipe grades) range from 50,000 to 500,000. Tensile strength properties generally range from 3 KPSI to 8 KPSI with elongations to break from 1 to 100%. The chemical properties of the extruded profile materials can vary depending upon the polymer end use applications. For example, polyethylene will have different chemical resistance from polybutylene or polyvinyl chloride.

Another material type is a bead material made from the compositions of the present invention. The bead material is particularly well suited for the production of products designed for controlled release of chemicals. Molecular weights of bead material typically ranges from 2,000 to 350,000.

A further material type is a colorant carrier made from the compositions of the present invention. The colorant carrier material is particularly useful as a carrier for, for example, inks, dyes, pigments, and toners. The colorant material can be produced by forming a solid resin using the polymer compositions of the present invention, adding desired additives such as pigments, inks, dyes, or toners, and grinding the solid resin plus additive to a desired particle size. Molecular weights of colorant carriers typically range from 5,000 to 1,500,000.

A further product type of the present invention includes powder materials. The powder materials can be produced by forming a solid resin using the polymer compositions of the present invention and grinding the solid resins to a desired particle size. Molecular weights of powder materials typically ranges from 2,000 to 1,000,000. Powder materials for coatings should have good adhesive properties when melted to the substrate onto which it is affixed. The material should have good flowability when melted in order to minimize pinholes in the coating. The chemical properties of the powder can vary based on the polymer and end use applications.

Additional information concerning suitable processes for preparing compositions of the present invention can be found in copending U.S. Applications No. 07/579,005 filed on September on Sep. 6, 1990 by Sinclair and No. 07/579,465 by Sinclair filed on Sep. 6, 1990, the contents of which are incorporated herein as if set forth in full.

MATERIAL PROPERTIES

The degradable polymer composition of the present invention has a wide variety of properties in addition to degradability which make the polymer composition useful in numerous end use applications. For example, by varying the concentration of the components or processing conditions of the degradable polymer composition, the properties of the composition can be varied. For example, those properties include toughness, flexibility, clarity, glossiness, adhesiveness, degradability, non-irritability, non-toxicity, water solubility, and heat shrinkability.

The materials of the present invention can be made more tough by including additives (i.e., modifiers or blended polymers) in the polymer composition having a high modulus of elasticity or by adjusting the amount of crosslinking of the polymer, such that the impact resistance of the polymer is increased to achieve desired levels.

The material of the present invention can also be made more flexible by increasing the amount of modification of the polymer composition by either internal or external modification which reduces the melt viscosity and/or lowers the glass transition temperature of the polymer composition thereby increasing the flexibility of the polymer composition to achieve standard desired levels.

Varying the amount of modification of the polymer compositions and the process conditions of the present invention also influences the discoloration of the polymer composition. Referring to co-pending U.S. patent application Ser. No. 07/579,465, the application discloses a polystyrene substitute being a clear and colorless composition. Increasing the amount of modification increases the clarity of the polymer composition by preventing heat build-up during processing of the polymer composition which may cause discoloration.

Varying the amount of modification of the polymer compositions also affects the glossiness of the polymer compositions. The glossiness of the polymer compositions is increased by altering the processing or the composition of the polymer compositions. For example, the polymer compositions may be processed using rough-surfaced molds or rough forming rolls to make the polymer less glossy.

The materials of the present invention can be made more adhesive by adjusting the amount of modification of the polymer composition. By increasing the amount of modification, the melting temperature of the polymer composition is lowered and the melt viscosity is lowered, thereby increasing the adhesiveness of the polymer composition.

The degradability of the polymer compositions can also be controlled according to the methods discussed in detail above.

The materials can be non-irritable and non-toxic by appropriate selection of starting materials for the polymer and any external modifiers.

The polymer compositions can be made heat shrinkable by, for example, orienting films without subsequently heat setting them, as described in detail above.

The polymer compositions can be made more water soluble by increasing the amount of water soluble co-monomers used in the polymer of the composition.

The polymer compositions used in materials of the present invention can also include other components, such as hydroscopic additives, pigments, heat stabilizers, antioxidants, UV light absorbers, hydrophobic additives, and insoluble additives. For example, hydroscopic additives can be added to give the composition selectively permeable qualities to compounds such as vapors, and to give the composition oil and surfactant resistance. Hydroscopic additives that can be added to the polymer composition include, for example, cellulosic compounds such as starches and wood flour. Pigments can be added to color the polymer compositions if desired. Pigments can be effectively combined with polymer compositions by use of conventional pigment and pigment carriers. Suitable pigments can include, for example, iron oxide, lead oxide, strontium, chromate, carbon black, coal dust, titanium dioxide, talc, barium sulfate, cadmium yellow, cadmium red, and chromium yellow. Heat stabilizers can be added to the polymer compositions to enable the compositions to be sterilizable without significant thermal degradation of the polymer compositions. Such heat stabilizers can include, for example, zinc stearate, zinc lactate and sodium citrate. Anti-oxidants can be added to prevent degradation of the compositions by free radicals produced by free radical generators such as ozone, gamma rays, and UV radiation. Anti-oxidants that can be added to the composition include, for example, pigments, sodium citrate, butylated hydroxy toluene, hydroquinones, and thiopropionates. UV light absorbers can be added to make the composition more resistant to degradation by ultraviolet radiation. Such UV radiation absorbers can include, for example, carbon black, zinc oxide and substituted benzophenones. Hydrophobic additives can be added to give the composition water resistance. Such hydrophobic additives include, for example, silicone, oils and waxes. Insoluble additives which migrate to the surface of the polymer composition can be added prior to polymerization to give the composition a clingy quality, such as for film-like wrapping materials. Such insoluble additives can include, for example, calcium carbonate, mica and wood flour.

PRODUCT TYPES

The degradable material of the present invention is useful in numerous product types because while the material is degradable, it is typically stable for a time sufficient to make it useful for a wide variety of applications.

The hydrolytically degradable material of the present invention is particularly useful for the production of absorbent articles. Absorbent articles can be produced by, for example, producing fibers out of the degradable polymer composition of the present invention which can be added to absorbent material to strengthen the material. Absorbent materials include materials able to absorb water, for example, material able to absorb at least about 50 percent of weight of the article's weight in water, more preferably at least about 500 percent of weight, and more preferably at least about 1,000 percent of weight. Such articles include, for example, towels, napkins, sponges, seed mats, seed strips, tissues, and toilet paper. Towels can include paper towels and multiple use towels similar to those sold under the trademark HANDI WIPES®[1]. [1]
Registered trademark of the Colgate-Palmolive Company, Registration No. 835,916.

Different material types of the hydrolytically degradable polymer composition of the present invention are particularly useful for the production of products for the controlled release of chemicals. Controlled release products include products for sustained release of chemicals and rapid release. Sustained release refers to the slow release of the chemicals contained in the product which differs from rapid release of chemicals in, for example, a sudden burst. Chemicals for controlled release can include biocides, fertilizers, attractants such as chemicals used to attract pests into traps, repellents, pharmaceuticals, detergents, dyes, microbes, foods, water, and fabric softeners. Chemicals can be microencapsulated or combined directly with the claimed polymer compositions and released slowly upon degradation of the polymer compositions. The rate of release of such chemicals from the polymer composition is dependent on the extent of degradability of the polymer composition used to make the product, the concentration of the active chemical on the product, and the method of association of the chemical with the product material.

Products for controlled release of chemicals can be produced from the bead-type material of the present invention including, for example, crowd control products including, for example, animal or people repellent products. Animal repellent products can be used to control, for example, vermin. People repellent products can be used to control, for example, criminals and crowds. Crowd control products include products such as tear gas release products. Other products for controlled release of chemicals include controlled release algaecides, controlled release mildewcides, controlled release of fungicides, water irrigation biocides, detergent delivery systems, shoe polishes, encapsulated microbes, fertilizers including house plant food, animal or fish food, deodorized kitty litter, plant waterers, bug repellents, tear gas, and water softeners. Products for controlled release of chemicals can be produced from the fiber-type material of the present invention including, for example, tree wrappings, and fabric softener delivery systems. Products for controlled release of chemicals can be produced from the film-type material of the present invention including, for example, preservative films, fragrance delivery systems, and food tenderizer film. Products for controlled release of chemicals can be produced from the injection molded-type material of the present invention including, for example, swimming pool conditioners, toilet bowl disinfectants, water line inserts, and chemical indicator strips for determining pH and color. Products for controlled release of chemicals can be produced from the extruded profile-type material of the present invention including, for example, flea collars.

The hydrolytically degradable materials of the present invention can be inherently flammable. Thus, the materials can be particularly useful for the production of flammable products including, for example, solid fuels and warning flares. The materials can be used with ignition systems.

The hydrolytically degradable material of the present invention are particularly useful for the production of oral drug delivery products, in particular capsules. The timing and rate of release of the drug contained in the delivery product is dependent on the degradability of the polymer composition used to produce the delivery product. The rate of release is also dependent on the concentration and form of the drug contained in the delivery product.

The adhesive-type hydrolytically degradable materials of the present invention are particularly useful for the production of adhesive products such as, backing adhesives, hot melt adhesives, and pressure sensitive adhesives. The adhesiveness of a product is dependent on the viscosity of the polymer composition and the amount of polymer composition used to produce the adhesive product. Such adhesives are typically used on a variety of products, including labels, envelopes, adhesive tapes, boxboard adhesive, bumper stickers, lint removers, and tear away strips.

The hydrolytically degradable materials of the present invention can be inherently oleophilic, if thermoset and heat resistant. Thermosets are made by including curable unsaturated polyesters in the present composition. Thus, the materials can be particularly useful for the production of lubricants including, for example, petroleum-based lubricants, graphite, fluorocarbons, silicones, natural waxes and oils, and lithium-based materials.

The hydrolytically degradable fiber material of the present invention is particularly useful for the production of filter products. Representative examples of suitable uses includes filters such as coffee filters and tea bags.

The hydrolytically degradable film-type material of the present invention is particularly useful for the production of a variety of specific bag-like products. Representative examples of suitable uses includes products such as weather balloons, and bags for compost, fertilizer, seed, sand, basting, food produce, cereals, snack chips, pet food, sandwiches, trash, carry-out, single serve condiments, newspaper, and medical disposal. The film-type material is also useful for producing multi-walled bags, liners for storage or shipping drums, Gaylord liners, plastic-lined paper bags for shipping and garbage, nonwoven filter bags, sanitary napkin and air sickness bags, and mesh bags. The toughness, flexibility, and degradability of the bags of the present invention will vary depending upon the requirements for specific product types. The toughness and flexibility of bags produced using the polymer composition of the present invention is dependent on the modifier concentration of the polymer composition. The rate of degradation of the bags is dependent on the degradability of the composition.

Products such as containers can be produced from a variety of material types of the hydrolytically degradable polymer composition of the present invention. Such material types have the characteristic of being selfstanding and include blow molded, coated paper, foam, injection molded, thermoformed and extruded profile types. The rigidity of the product is dependent on the molecular weight and concentration of modifier used to produce the polymer composition. Representative suitable uses include food, including fast food, egg cartons, frozen dinner, drink, dairy and produce containers, bottles, jugs, shipping or storage drums, automotive and marine oil containers, containers used for camping, photographic film containers, mailing tubes, caulk tubes, laundry powder containers, plastic envelopes, egg cartons, trays for meat, audio and visual cassettes, compact disk cassettes, jewelry containers, cigarette lighters, marine food service, tampon applicators, cosmetic containers, razor blade dispensers, shotgun shells, shotgun shell holders, oven pans, toner cartridges, paint can lids, and deli and food storage containers.

The film-type material of the present invention is also useful as packaging material such as, for example, butcher and deli paper, film wrap, microwave cooking papers, gift wrap paper, bows and cards, rings for six packs of cans and bottles, cigarette packaging, floral wrap, motel and hotel glass wraps, blister packs, shrinkable wraps, bottle cap safety tamper evident wrap, plastic windows for viewing package contents such as windows for envelopes, print films for packaging, food product packages and toiletry packages, vending machine packaging, and foam fill dunnage. The protective quality of the packaging material is dependent on, for example, the toughness, flexibility, and heat shrinkability of the polymer composition used to produce the product.

The film, woven and non-woven material types of the hydrolytically degradable polymer composition of the present invention is useful in the production of clothing such as coats, pants, gloves, hats, shoes, boots, inner and outer layers of diapers, masks, pantyhose, and ponchos. Such clothing are particularly suitable in situations where disposable clothing is needed such as in hospital use, sterile work, janitorial work, work involving dangerous compounds such as radioactivity or toxic chemicals, and in research laboratories. The protective nature of the clothing product is dependent on the toughness of the polymer composition used to produce the product.

The hydrolytically degradable polymer composition of the present invention is useful as an additive in the production of paper products including, for example, junk mail, price tags, release liners for adhesive products, cardboard boxes, paper food containers, and signs. Addition of the polymer composition to conventional paper products increases the durability by increasing the wet strength of the paper. The degradability of the paper product is dependent on the amount and degradability of the polymer composition added to the paper. Typically such paper products can include between about 0.5 and about 10 weight percent of polymer composition. The hydrolytically degradable property facilitates recycling of mixed material products such as paper plastic laminates. The laminates can be recycled by solubilizing the hydrolytically degradable polymer with an alkali wash and then recycling the solid paper fiber from the liquid monomer of the polymer composition.

A variety of material types of the hydrolytically degradable polymer compositions of the present invention can be added to health products. A film-like material type can be used to produce health products such as bedding products for hospital applications, pet cage liners, deodorant pads, feminine hygiene napkins, seat covers, and bandages. A foam-like material type can be used to produce personal and home care products such as hair products, scrubbers, sponges, and mops. A fiber-like material type can be used to produce health products such as dental floss and toothbrushes. An injection-molded material type can be used to produce health products such as tooth paste containers, mouthpieces for thermometers, syringes, micropipette tips, combs and hairbrushes, curlers, shavers, and waterpick tips. An extruded profile material type can be used to produce health products such as supports for cotton swabs. An open pot molded material type can be used to produce health products such as contact lenses.

A variety of material types of the hydrolytically degradable polymer compositions of the present invention can be used to produce health products that need to be autoclaved prior to disposal. Contaminated solid health products produced using the polymer composition of the present invention can be heated at high temperatures to form sterile liquids for efficient disposal. Such health products include for example, surgical and patient gowns, operating table and examination table sheets, intravenous tubing, catheter tubing, needles, syringes, bags for body fluids such as blood and plasma, and other disposable hospital supply goods.

A variety of material types of the hydrolytically degradable polymer compositions of the present invention can be used to produce substrates suitable for attachment and/or growth of living cells. Such substrates can be products for in vivo and/or in vitro growth of cells. As used herein, the term "in vitro" refers to the growth of cells in an artificial environment. Without being bound by theory, it is believed that living cells are able to attach and/or maintain cellular functions, such as growth and/or production of metabolites and proteins, due to: the morphology of the surface; the relative hydrophilic HLB; the ionic surface characteristics of the polymer composition of the present invention. As such, substrates produced using the polymer composition of the present invention are useful, for example, for: growing skin cells for transplantation or in vitro testing of compounds frequently encountered by skin such as cosmetics and lotions; growing retinal cells for testing contact lens products; growing cells capable of producing useful cellular products such as proteins, nucleic acids and carbohydrates useful as pharmaceuticals and diagnostics; growing hematopoietic cells for transplantation; growing hair follicle cells for transplantation; and growing chondroblasts and osteoblasts for reconstruction of cartilage and bone.

The polymer compositions of the present invention can be used to produce material types selected from injection-molded products, fibers, extruded and molded products, laminates, foams, powders and coatings, to produce substrate products of variable dimensions suitable for culturing living cells, including dishes, trays, sheets, flasks, slides, beads, tubes, filters and bottles.

Consumer products can be produced from a variety of material types of the hydrolytically degradable polymer composition of the present invention. A film-like material type can be used to produce home products such as tablecloths, placemats, shower curtains, artificial Christmas trees, and Christmas tinsel. A fiber-like material type can be used to produce home products such as pipe cleaners. An injection molded material type can be used to produce home products such as toys for children and adults, paper clips, disposable camera bodies and lenses, and popsicle sticks. An extruded profile material type is used to produce consumer products such as pens and pencils, shopping carts, fishing gear, camping gear, circuit breakers, twist-tie fasteners, pins, straws, toothpicks, and credit cards. A laminate material type can be used to produce consumer products such as mouse traps, roach traps, and disposable dinnerware.

Garden products can be produced from a variety of material types of the hydrolytically degradable polymer composition of the present invention. A film-like material type can be used to produce a garden product such as root ball cover, geo-textile erosion control, weed control film, mulch, seed mats, and seed strips. An injection molded material type can be used to produce a garden product such as starter pots for plants, and, for example, seedling pots and substrates used in the culture of plants by cloning. An extruded profile type can be used to produce garden products such as fencing stakes, garden marker stakes, and plant stakes.

The hydrolytically degradable polymer composition of the present invention is also particularly useful for producing automobile parts such as tires and automobile interior parts. The ability to mold such products is dependent on comonomer ratio, molecular weight of the polymer product, and the choice and percentage of modifier added to the polymer composition to produce the automobile part. In addition, the tackiness and adhesive strength required in automobile parts is dependent on the concentration of modifier in the polymer composition.

The hydrolytically degradable polymer composition of the present invention is also particularly useful for producing products for construction such as construction plastics and highway crack inducers. The film and extruded profile material types are particularly useful for the production of such construction products. The toughness of the construction products is dependent on the concentration of modifier added to the polymer composition used to produce the construction product.

The hydrolytically degradable polymer composition of the present invention is also particularly useful for producing netting products. The fiber-type material of the present invention can be used to produce products such as netting, such as fish netting, erosion control landscape netting and load consolidation netting. The strength of the netting product is dependent on the amount of modifier added to the polymer composition used to produce the netting.

The hydrolytically degradable polymer composition of the present invention is also particularly useful for producing rope products. The fiber-type material of the present invention is added to produce products such as twine, bale banding, and ropes. The strength of the rope product is dependent on the amount of modifier added to the polymer composition used to produce the rope.

The hydrolytically degradable polymer composition of the present invention is also particularly useful for producing monofilament and multifilament products. The fiber-type material of the present invention is also useful for the production of the monofilament and multifilament of paper towels.

The hydrolytically degradable polymer composition of the present invention is also particularly useful for producing polymer resins which act as degradable replacements for products such as polyvinylchloride, polyethylene terepthalate, crystal polystyrene, impact-modified polystyrene, low density polyethylene, linear low density polyethylene, and expandable polystyrene.

What is claimed:

1. An adhesive product comprising a hydrolytically degradable polymer and a modifier, wherein said modifier is compatible with said polymer and is non-volatile and non-fugitive and wherein said polymer comprises repeating monomer or comonomer units selected from the group consisting of:

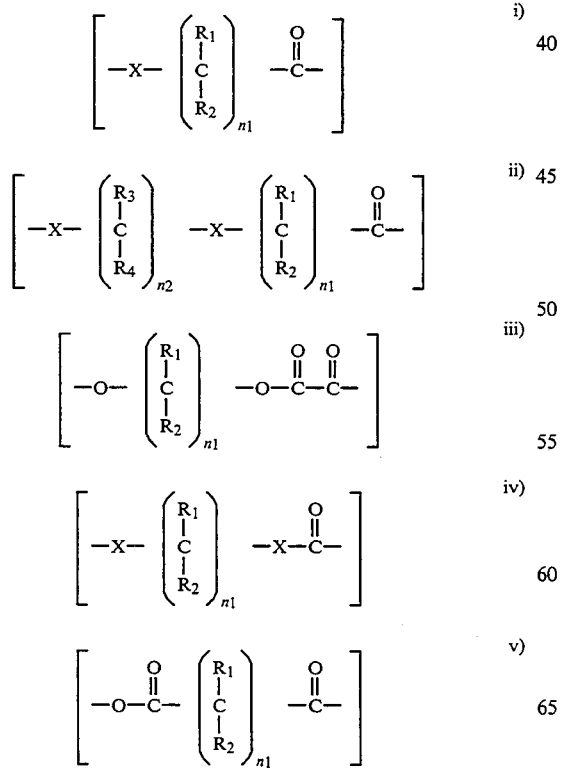

wherein X is the same or different and is O or NR' with R' being the same or different and being H, hydrocarbyl, or substituted hydrocarbyl; $R_1$, $R_2$, $R_3$ and $R_4$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1–12.

2. The adhesive product of claim 1, wherein said degradable polymer comprises polylactic acid.

3. The adhesive product of claim 1, wherein said degradable polymer comprises at least about 50 weight percent repeating units derived from lactic acid or lactide.

4. An adhesive product comprising a hydrolytically degradable polymer, said polymer comprising:
   (a) a backbone chain;
   (b) first repeating units of the formula

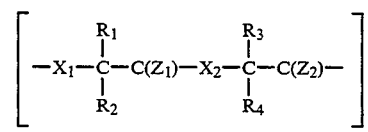

where, independently for each such first repeating unit:
   $X_1$ and $X_2$ are independently O or NR' and R' is independently H, hydrocarbyl, substituted hydrocarbyl or a hydrocarbyl derivative; $R_1$, $R_2$ and $Z_1$ combined have at most one carbon atom; $R_3$, $R_4$ and $Z_2$ combined have at most one carbon atom; $Z_1$ and $Z_2$ are each independently one or more constituent group extending from the backbone chain and being covalently bonded to an associated carbon atom in the backbone chain, at least one of $Z_1$ and $Z_2$ being oxygen which forms a carbonyl group with the associated carbon atom in the backbone chain; and the molecular weight of such a first repeating unit is less than about 145; and
   (c) from about 1 weight percent to about 50 weight percent, based on the total weight of said polymer, of second repeating units of the formula

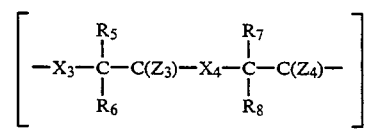

where, independently for each such second repeating unit:
   $X_3$ and $X_4$ are independently O or NR' and R' is independently H, hydrocarbyl, substituted hydrocarbyl or a hydrocarbyl derivative; $R_5$, $R_6$, $R_7$ and $R_8$ combined have at least four carbon atoms; $Z_3$ and $Z_4$ are each independently one or more constituent group extending from the backbone chain and being covalently bonded to an associated carbon atom in the backbone chain, at least one of $Z_3$ and $Z_4$ being oxygen which forms a carbonyl group with the associated carbon atom in the backbone chain.

5. The adhesive product of claim 4, wherein said first repeating units are derived from lactic acid or lactide.

6. A flammable product comprising a hydrolytically degradable polymer and a modifier, wherein said modifier is compatible with said polymer and is non-volatile and non-fugitive and wherein said polymer comprises repeating monomer or comonomer units selected from the group consisting of:

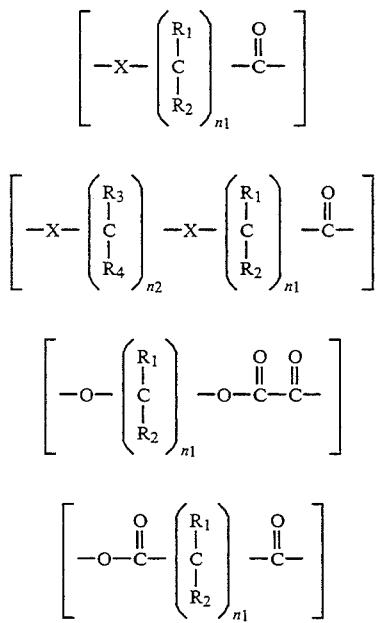

i)

ii)

iii)

iv)

wherein X is the same or different and is O or NR4 with R' being the same or different and being H, hydrocarbyl, or substituted hydrocarbyl; $R_1$, $R_2$, $R_3$ and $R_4$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1-12.

7. A flammable product comprising a hydrolytically degradable polymer, said polymer comprising:
(a) a backbone chain;
(b) first repeating units of the formula

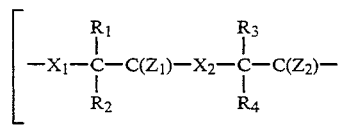

where, independently for each such first repeating unit:
$X_1$ and $X_2$ are independently O or NR' and R' is independently H, hydrocarbyl, substituted hydrocarbyl or a hydrocarbyl derivative; $R_1$, $R_2$ and $Z_1$ combined have at most one carbon atom; $R_3$, $R_4$ and $Z_2$ combined have at most one carbon atom; $Z_1$ and $Z_2$ are each independently one or more constituent group extending from the backbone chain and being covalently bonded to an associated carbon atom in the backbone chain, at least one of $Z_1$ and $Z_2$ being oxygen which forms a carbonyl group with the associated carbon atom in the backbone chain; and the molecular weight of such a first repeating unit is less than about 145; and
(c) from about 1 weight percent to about 50 weight percent, based on the total weight of said polymer, of second repeating units of the formula

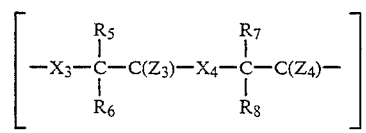

where, independently for each such second repeating unit:
$X_3$ and $X_4$ are independently O or NR' and R' is independently H, hydrocarbyl, substituted hydrocarbyl or a hydrocarbyl derivative; $R_5$, $R_6$, $R_7$ and $R_8$ combined have at least four carbon atoms; $Z_3$ and $Z_4$ are each independently one or more constituent group extending from the backbone chain and being covalently bonded to an associated carbon atom in the backbone chain, at least one of $Z_3$ and $Z_4$ being oxygen which forms a carbonyl group with the associated carbon atom in the backbone chain.

8. A packaging product comprising a hydrolytically degradable polymer and a modifier, wherein said modifier is compatible with said polymer and is non-volatile and non-fugitive and wherein said polymer comprises repeating monomer or comonomer units selected from the group consisting of:

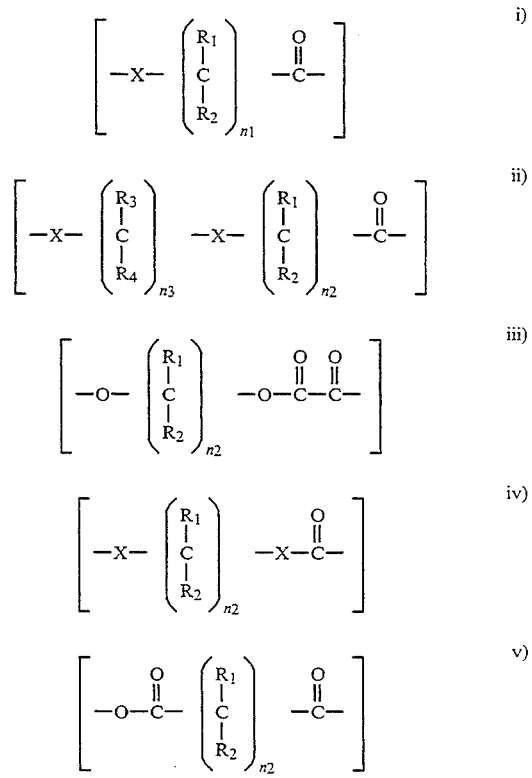

i)

ii)

iii)

iv)

v)

wherein X is the same or different and is O or NR' with R' being the same or different and being H, hydrocarbyl, or substituted hydrocarbyl; $R_1$, $R_2$, $R_3$ and $R_4$ can be the same or different and are hydrogen, hydrocarbyl containing 1 to 24 carbon atoms, or substituted hydrocarbyl containing 1 to 24 carbon atoms, where $n_1$ is 1 or 2 and where $n_2$ and $n_3$ can be the same or different and are an integer of from 1-12.

9. A packaging product comprising a hydrolytically degradable polymer, said polymer comprising:

(a) a backbone chain;
(b) first repeating units of the formula

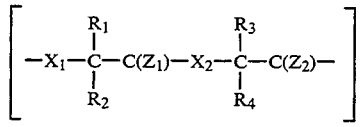

where, independently for each such first repeating unit:
X$_1$ and X$_2$ are independently O or NR' and R' is independently H, hydrocarbyl, substituted hydrocarbyl or a hydrocarbyl derivative; R$_1$, R$_2$ and Z$_1$ combined have at most one carbon atom; R$_3$, R$_4$ and Z$_2$ combined have at most one carbon atom; Z$_1$ and Z$_2$ are each independently one or more constituent group extending from the backbone chain and being covalently bonded to an associated carbon atom in the backbone chain, at least one of Z$_2$ and Z$_2$ being oxygen which forms a carbonyl group with the associated carbon atom in the backbone chain; and the molecular weight of such a first repeating unit is less than about 145; and (c) from about 1 weight percent to about 50 weight percent, based on the total weight of said polymer, of second repeating units of the formula

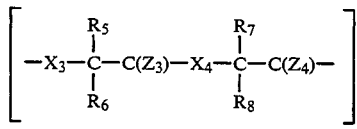

where, independently for each such second repeating unit:
X$_3$ and X$_4$ are independently O or NR' and R' is independently H, hydrocarbyl, substituted hydrocarbyl or a hydrocarbyl derivative; R$_5$, R$_6$, R$_7$ and R$_8$ combined have at least four carbon atoms; Z$_3$ and Z$_4$ are each independently one or more constituent group extending from the backbone chain and being covalently bonded to an associated carbon atom in the backbone chain, at least one of Z$_3$ and Z$_4$ being oxygen which forms a carbonyl group with the associated carbon atom in the backbone chain.

10. A clothing product comprising a hydrolytically degradable polymer and a modifier, wherein said modifier is compatible with said polymer and is non-volatile and non-fugitive and wherein said polymer comprises repeating monomer or comonomer units selected from the group consisting of:

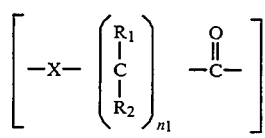

i)

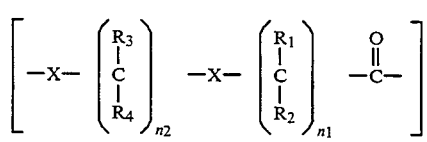

ii)

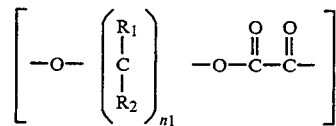

iii)

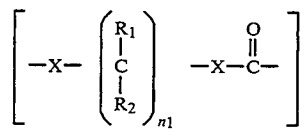

iv)

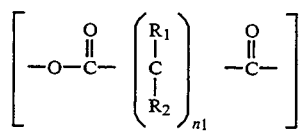

v)

wherein X is the same or different and is O or NR' with R' being the same or different and being hydrocarbyl, or substituted hydrocarbyl; R$_1$, R$_2$, R$_3$ and R$_4$ can be the same or different and are hydrogen, hydrocarbyl containing 1 to 24 carbon atoms, or substituted hydrocarbyl containing 1 to 24 carbon atoms, and where n$_1$ and n$_2$ can be the same or different and are an integer of from 1-12.

11. A clothing product comprising a hydrolytically degradable polymer, said polymer comprising:
(a) a backbone chain;
(b) first repeating units of the formula

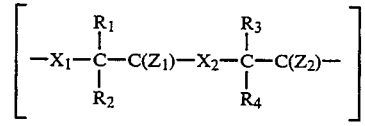

where, independently for each such first repeating unit:
X$_1$ and X$_2$ are independently O or NR' and R' is independently H, hydrocarbyl, substituted hydrocarbyl or a hydrocarbyl derivative; R$_1$, R$_2$ and Z$_1$ combined have at most one carbon atom; R$_3$, R$_4$ and Z$_2$ combined have at most one carbon atom; Z$_1$ and Z$_2$ are each independently one or more constituent group extending from the backbone chain and being covalently bonded to an associated carbon atom in the backbone chain, at least one of Z$_1$ and Z$_2$ being oxygen which forms a carbonyl group with the associated carbon atom in the backbone chain; and the molecular weight of such a first repeating unit is less than about 145; and (c) from about 1 weight percent to about 50 weight percent, based on the total weight of said polymer, of second repeating units of the formula

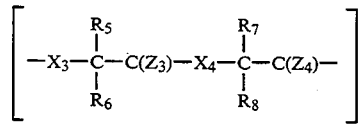

where, independently for each such second repeating unit:
X$_3$ and X$_4$ are independently O or NR' and R' is independently H, hydrocarbyl, substituted hydrocarbyl or a hydrocarbyl derivative; $R_5$, $R_6$, $R_7$ and $R_8$ combined have at least four carbon atoms; $Z_3$ and $Z_4$ are each independently one or more constituent group extending from the backbone chain and being covalently bonded to an associated carbon atom in the backbone chain, at least one of $Z_3$ and $Z_4$ being oxygen which forms a carbonyl group with the associated carbon atom in the backbone chain.

12. A garden product comprising a hydrolytically degradable polymer and a modifier, wherein said modifier is compatible with said polymer and is non-volatile and non-fugitive and wherein said polymer comprises repeating monomer or comonomer units selected from the group consisting of:

i)
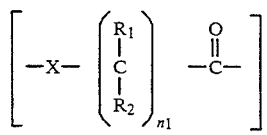

ii)
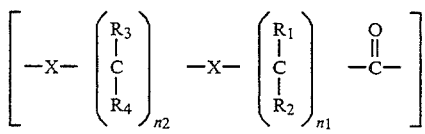

iii)
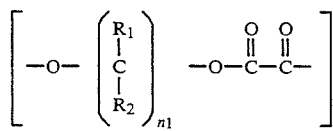

iv)
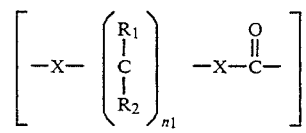

v)
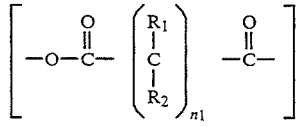

wherein X is the same or different and is O or NR' with R' being the same or different and being H, hydrocarbyl, or substituted hydrocarbyl; $R_1$, $R_2$, $R_3$ and $R_4$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1–12.

13. A garden product comprising a hydrolytically degradable polymer, said polymer comprising:
(a) a backbone chain;
(b) first repeating units of the formula

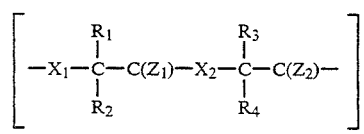

where, independently for each such first repeating unit:
$X_1$ and $X_2$ are independently O or NR' and R' is independently H, hydrocarbyl, substituted hydrocarbyl or a hydrocarbyl derivative; $R_1$, $R_2$ and $Z_1$ combined have at most one carbon atom; $R_3$, $R_4$ and $Z_2$ combined have at most one carbon atom; $Z_1$ and $Z_2$ are each independently one or more constituent group extending from the backbone chain and being covalently bonded to an associated carbon atom in the backbone chain, at least one of $Z_1$ and $Z_2$ being oxygen which forms a carbonyl group with the associated carbon atom in the backbone chain; and the molecular weight of such a first repeating unit is less than about 145; and (c) from about 1 weight percent to about 50 weight percent, based on the total weight of said polymer, of second repeating units of the formula

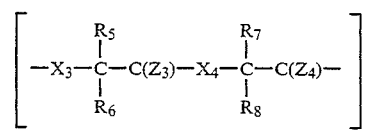

where, independently for each such second repeating unit:
$X_3$ and $X_4$ are independently O or NR' and R' is independently H, hydrocarbyl, substituted hydrocarbyl or a hydrocarbyl derivative; $R_5$, $R_6$, $R_7$ and $R_8$ combined have at least four carbon atoms; $Z_3$ and $Z_4$ are each independently one or more constituent group extending from the backbone chain and being covalently bonded to an associated carbon atom in the backbone chain, at least one of $Z_3$ and $Z_4$ being oxygen which forms a carbonyl group with the associated carbon atom in the backbone chain.

14. A filter comprising a hydrolytically degradable polymer and a modifier, wherein said modifier is compatible with said polymer and is non-volatile and non-fugitive and wherein said polymer comprises repeating monomer or comonomer units selected from the group consisting of:

i)
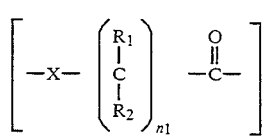

ii)
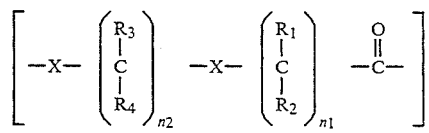

iii)
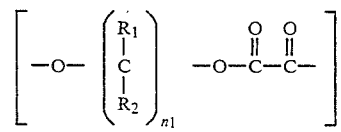

iv)
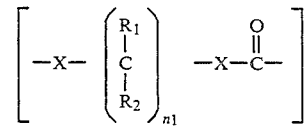

-continued v)
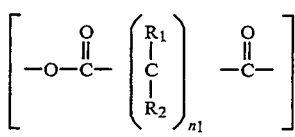

wherein X is the same or different and is O or NR' with R' being the same or different and being H, hydrocarbyl, or substituted hydrocarbyl; $R_1$, $R_2$, $R_3$ and $R_4$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1–12.

15. A filter comprising a hydrolytically degradable polymer, said polymer comprising:
   (a) a backbone chain;
   (b) first repeating units of the formula

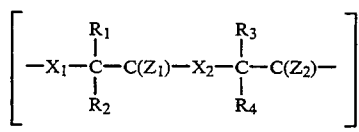

where, independently for each such first repeating unit:
   $X_1$ and $X_2$ are independently O or NR' and R' is independently H, hydrocarbyl, substituted hydrocarbyl or a hydrocarbyl derivative; $R_1$, $R_2$ and $Z_1$ combined have at most one carbon atom; $R_3$, $R_4$ and $Z_2$ combined have at most one carbon atom; $Z_1$ and $Z_2$ are each independently one or more constituent group extending from the backbone chain and being covalently bonded to an associated carbon atom in the backbone chain, at least one of $Z_1$ and $Z_2$ being oxygen which forms a carbonyl group with the associated carbon atom in the backbone chain; and the molecular weight of such a first repeating unit is less than about 145; and
   (c) from about 1 weight percent to about 50 weight percent, based on the total weight of said polymer, of second repeating units of the formula

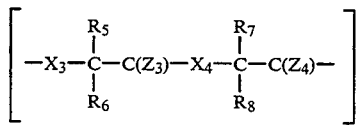

where, independently for each such second repeating unit:
   $X_3$ and $X_4$ are independently O or NR' and R' is independently H, hydrocarbyl, substituted hydrocarbyl or a hydrocarbyl derivative; $R_5$, $R_6$, $R_7$ and $R_8$ combined have at least four carbon atoms; $Z_3$ and $Z_4$ are each independently one or more constituent group extending from the backbone chain and being covalently bonded to an associated carbon atom in the backbone chain, at least one of $Z_3$ and $Z_4$ being oxygen which forms a carbonyl group with the associated carbon atom in the backbone chain.

16. A bag comprising a hydrolytically degradable polymer and a modifier, wherein said modifier is compatible with said polymer and is non-volatile and non-fugitive and wherein said polymer comprises repeating monomer or comonomer units selected from the group consisting of:

i)
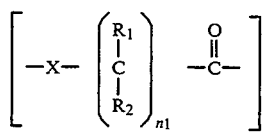

ii)
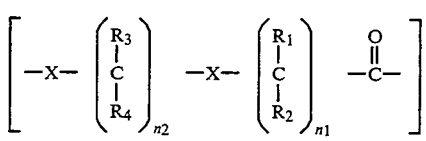

iii)
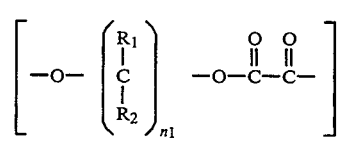

iv)
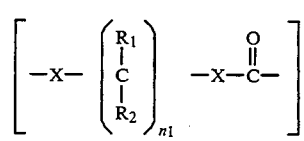

v)
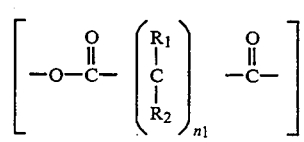

wherein X is the same or different and is O or NR' with R' being the same or different and being H, hydrocarbyl, or substituted hydrocarbyl; $R_1$, $R_2$, $R_3$ and $R_4$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1–12.

17. A bag comprising a hydrolytically degradable polymer, said polymer comprising:
   (a) a backbone chain;
   (b) first repeating units of the formula

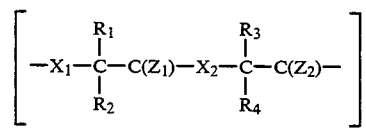

where, independently for each such first repeating unit:
   $X_1$ and $X_2$ are independently O or NR' and R' is independently H, hydrocarbyl, substituted hydrocarbyl or a hydrocarbyl derivative; $R_1$, $R_2$ and $Z_1$ combined have at most one carbon atom; $R_3$, $R_4$ and $Z_2$ combined have at most one carbon atom; $Z_1$ and $Z_2$ are each independently one or more constituent group extending from the backbone chain and being covalently bonded to an associated carbon atom in the backbone chain, at least one of $Z_1$ and $Z_2$ being oxygen which forms a carbonyl group with the associated carbon atom in the backbone chain; and the molecular weight of such a first repeating unit is less than about 145; and (c) from about 1 weight percent to about 50 weight percent, based on the total weight of said polymer, of second repeating units of the formula

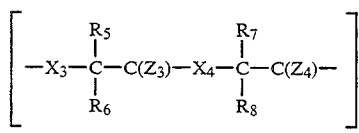

where, independently for each such second repeating unit:

X$_3$ and X$_4$ are independently O or NR' and R' is independently H, hydrocarbyl, substituted hydrocarbyl or a hydrocarbyl derivative; R$_5$, R$_6$, R$_7$ and R$_8$ combined have at least four carbon atoms; Z$_3$ and Z$_4$ are each independently one or more constituent group extending from the backbone chain and being covalently bonded to an associated carbon atom in the backbone chain, at least one of Z$_3$ and Z$_4$ being oxygen which forms a carbonyl group with the associated carbon atom in the backbone chain.

18. A container comprising a hydrolytically degradable polymer and a modifier wherein said modifier is compatible with said polymer and is non-volatile and non-fugitive and wherein said polymer comprises repeating monomer or comonomer units selected from the group consisting of:

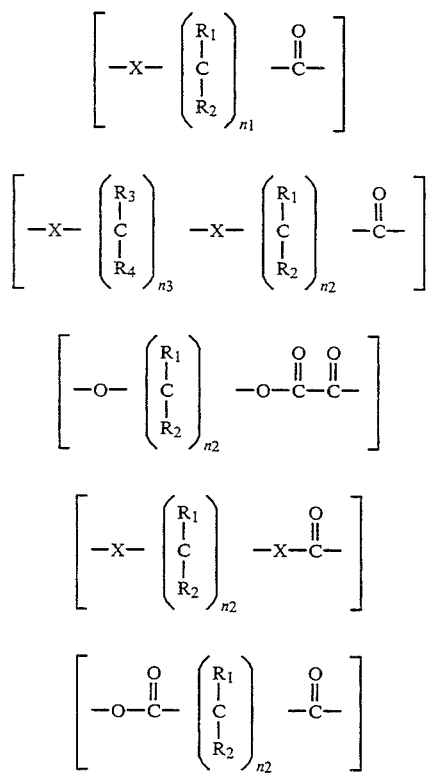

wherein X is the same or different and is O or NR' with R' being the same or different and being H, hydrocarbyl, or substituted hydrocarbyl; R$_1$, R$_2$, R$_3$ and R$_4$ can be the same or different and are hydrogen, hydrocarbyl containing 1 to 24 carbon atoms, or substituted hydrocarbyl containing 1 to 24 carbon atoms, where n$_1$ is 1 or 2 and where n$_2$ and n$_3$ can be the same or different and are an integer of from 1–12.

19. A container comprising a hydrolytically degradable polymer, said polymer comprising:
(a) a backbone chain;
(b) first repeating units of the formula

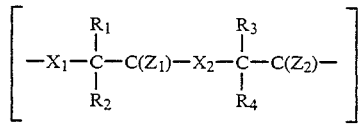

where, independently for each such first repeating unit:

X$_1$ and X$_2$ are independently O or NR' and R' is independently H, hydrocarbyl, substituted hydrocarbyl or a hydrocarbyl derivative; R$_1$, R$_2$ and Z$_1$ combined have at most one carbon atom; R$_3$, R$_4$ and Z$_2$ combined have at most one carbon atom; Z$_1$ and Z$_2$ are each independently one or more constituent group extending from the backbone chain and being covalently bonded to an associated carbon atom in the backbone chain, at least one of Z$_1$ and Z$_2$ being oxygen which forms a carbonyl group with the associated carbon atom in the backbone chain; and the molecular weight of such a first repeating unit is less than about 145; and (c) from about 1 weight percent to about 50 weight percent, based on the total weight of said polymer, of second repeating units of the formula

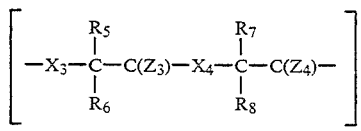

where, independently for each such second repeating unit:

X$_3$ and X$_4$ are independently O or NR' and R' is independently H, hydrocarbyl, substituted hydrocarbyl or a hydrocarbyl derivative; R$_5$, R$_6$, R$_7$ and R$_8$ combined have at least four carbon atoms; Z$_3$ and Z$_4$ are each independently one or more constituent group extending from the backbone chain and being covalently bonded to an associated carbon atom in the backbone chain, at least one of Z$_3$ and Z$_4$ being oxygen which forms a carbonyl group with the associated carbon atom in the backbone chain.

20. A coating comprising a hydrolytically degradable polymer and a modifier wherein said modifier is compatible with said polymer and is non-volatile and non-fugitive and wherein said polymer comprises repeating monomer or comonomer units selected from the group consisting of:

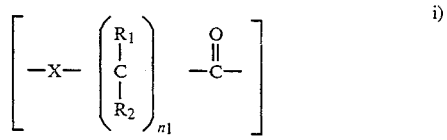

-continued

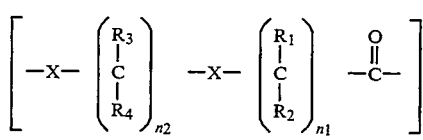 ii)

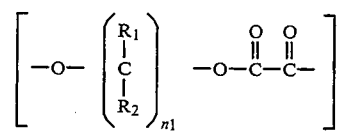 iii)

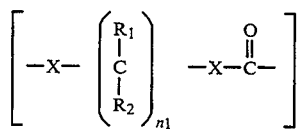 iv)

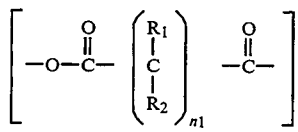 v)

wherein X is the same or different and is O or NR' with R' being the same or different and being H, hydrocarbyl, or substituted hydrocarbyl; $R_1$, $R_2$, $R_3$ and $R_4$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1-12.

21. A coating comprising a hydrolytically degradable polymer, said polymer comprising:
(a) a backbone chain;
(b) first repeating units of the formula

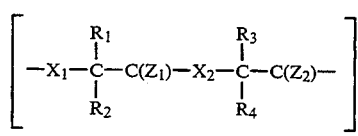

where, independently for each such first repeating unit:
$X_1$ and $X_2$ are independently O or NR' and R' is independently H, hydrocarbyl, substituted hydrocarbyl or a hydrocarbyl derivative; $R_1$, $R_2$ and $Z_1$ combined have at most one carbon atom; $R_3$, $R_4$ and $Z_2$ combined have at most one carbon atom; $Z_1$ and $Z_2$ are each independently one or more constituent group extending from the backbone chain and being covalently bonded to an associated carbon atom in the backbone chain, at least one of $Z_1$ and $Z_2$ being oxygen which forms a carbonyl group with the associated carbon atom in the backbone chain; and the molecular weight of such a first repeating unit is less than about 145; and
(c) from about 1 weight percent to about 50 weight percent, based on the total weight of said polymer, of second repeating units of the formula

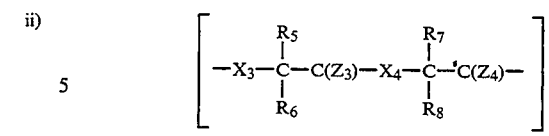

where, independently for each such second repeating unit:
$X_3$ and $X_4$ are independently O or NR' and R' is independently H, hydrocarbyl, substituted hydrocarbyl or a hydrocarbyl derivative; $R_5$, $R_6$, $R_7$ and $R_8$ combined have at least four carbon atoms; $Z_3$ and $Z_4$ are each independently one or more constituent group extending from the backbone chain and being covalently bonded to an associated carbon atom in the backbone chain, at least one of $Z_3$ and $Z_4$ being oxygen which forms a carbonyl group with the associated carbon atom in the backbone chain.

22. A substrate suitable for the growth of cells, said substrate selected from the group consisting of injection-molded material types, fibers, extruded and molded material types, laminates, foams, powders and caotings, wherein said substrate comprises a hydrolytically degradable polymer and a modifier wherein said modifier is compatible with said polymer and is non-volatile and non-fugitive and wherein said polymer comprises repeating monomer or comonomer units selected from the group consisting of:

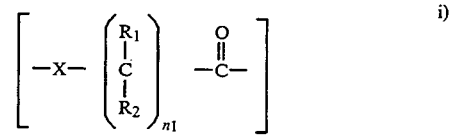 i)

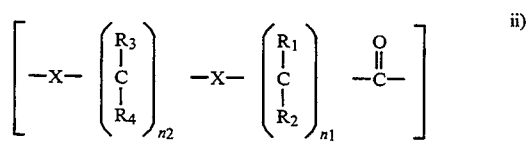 ii)

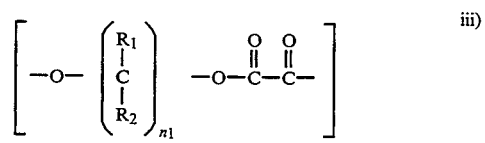 iii)

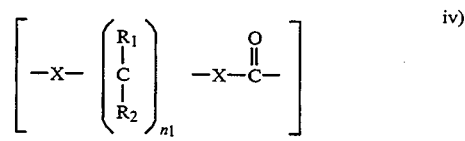 iv)

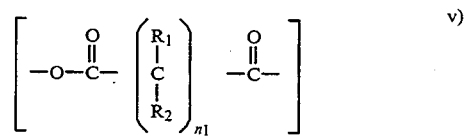 v)

wherein X is the same or different and is O or NR' with R' being the same or different and being H, hydrocarbyl, or substituted hydrocarbyl; $R_1$, $R_2$, $R_3$ and $R_4$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1-12.

* * * * *

UNITED STATES PATENT AND TRADEMARK OFFICE
CERTIFICATE OF CORRECTION

PATENT NO. : 5,444,113
DATED : August 22, 1995
INVENTOR(S) : Sinclair et al.

It is certified that error appears in the above-identified patent and that said Letters Patent is hereby corrected as shown below:

Col. 41:
In Claim 6, line 31, please delete "NR4" and insert therefor --NR'--.

Col. 43:
In Claim 9, line 21, please delete the first occurrence of "$Z_2$" and insert therefor --$Z_1$--.

Col. 48:
In Claim 17, line 65, please delete "$Z_1$ and $z_2$" and insert therefor --$Z_1$ and $Z_2$--.

Col. 50:
In Claim 18, line 1, please delete "$n_1$is" and insert therefor --$n_1$ is--.

Col. 52:
In Claim 22, line 23, please delete "caotings" and insert therefor --coatings--.

Signed and Sealed this

Third Day of November, 1998

Attest:

BRUCE LEHMAN

*Attesting Officer*    *Commissioner of Patents and Trademarks*